(12) United States Patent
Jung et al.

(10) Patent No.: US 10,697,665 B2
(45) Date of Patent: *Jun. 30, 2020

(54) AIR CLEANER

(71) Applicant: LG ELECTRONICS INC., Seoul (KR)

(72) Inventors: Soonki Jung, Seoul (KR); Hyunpil Ha, Seoul (KR); Yeongcheol Mun, Seoul (KR); Jaekyun Park, Seoul (KR); Soohyun Bae, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/409,017

(22) Filed: May 10, 2019

(65) Prior Publication Data

US 2019/0264948 A1    Aug. 29, 2019

Related U.S. Application Data

(63) Continuation of application No. 15/441,957, filed on Feb. 24, 2017, now Pat. No. 10,323,855.

(30) Foreign Application Priority Data

Feb. 26, 2016  (KR) .......................... 10-2016-0023663
Oct. 25, 2016  (KR) .......................... 10-2016-0139376
Dec. 15, 2016  (KR) .......................... 10-2016-0171724

(51) Int. Cl.
*B01D 29/56* (2006.01)
*B01D 46/42* (2006.01)
(Continued)

(52) U.S. Cl.
CPC ................. *F24F 11/89* (2018.01); *A61L 2/22* (2013.01); *B01D 46/002* (2013.01);
(Continued)

(58) Field of Classification Search
CPC .... B01D 29/56; B01D 46/002; B01D 46/008; B01D 46/0019; B01D 46/42;
(Continued)

(56) References Cited

U.S. PATENT DOCUMENTS 4,365,980 A    12/1982  Culbert et al.
4,905,340 A     3/1990  Gutschrnit
(Continued)

FOREIGN PATENT DOCUMENTS

CN    1487246    4/2004
CN    1510348    7/2004
(Continued)

OTHER PUBLICATIONS

U.S. Appl. No. 15/363,438, filed Nov. 29, 2016.
(Continued)

*Primary Examiner* — Minh Chau T Pham
(74) *Attorney, Agent, or Firm* — KED & Associates LLP

(57) ABSTRACT

An air cleaner is provided. The air cleaner may include at least one air cleaning module including a fan, a filter and an inlet through which air is suctioned into the filter; an air flow controller configured to be movably disposed on the at least one air cleaning module and including an air flow control fan to control a flow of the air discharged from the at least one air cleaning module. The air flow controller may be movable from a first position at which the air is discharged in an upward direction to a second position at which the air is discharged in a diagonally upward direction.

20 Claims, 30 Drawing Sheets

(51) Int. Cl.

| | | |
|---|---|---|
| *B23P 17/04* | (2006.01) | |
| *F24F 11/89* | (2018.01) | |
| *A61L 2/22* | (2006.01) | |
| *F24F 13/12* | (2006.01) | |
| *F24F 13/14* | (2006.01) | |
| *F24F 3/16* | (2006.01) | |
| *B01D 46/00* | (2006.01) | |
| *F24F 1/0071* | (2019.01) | |
| *B01D 46/24* | (2006.01) | |
| *F24F 13/20* | (2006.01) | |

(52) U.S. Cl.
CPC ..... *B01D 46/0008* (2013.01); *B01D 46/0019* (2013.01); *B01D 46/0047* (2013.01); *B01D 46/24* (2013.01); *B01D 46/2403* (2013.01); *F24F 1/0071* (2019.02); *F24F 3/1603* (2013.01); *F24F 13/12* (2013.01); *F24F 13/14* (2013.01); *A61L 2209/11* (2013.01); *A61L 2209/12* (2013.01); *A61L 2209/14* (2013.01); *B01D 2273/30* (2013.01); *F24F 2013/205* (2013.01)

(58) Field of Classification Search
CPC ............ B01D 46/0021; B01D 46/2411; B01D 2273/30; B23P 17/04; Y10T 29/49826; F24F 3/1603; F24F 11/89; A61L 2/22; A61L 2209/11
USPC ...... 55/356, 385.1, 461, 471, 473, 481, 483, 55/456, 445, 448, 449, 457; 96/224; 29/428
See application file for complete search history.

(56) References Cited

U.S. PATENT DOCUMENTS

| | | | |
|---|---|---|---|
| 5,117,652 A | 6/1992 | Takeuchi et al. | |
| 5,264,015 A | 11/1993 | Matsui | |
| 5,334,248 A | 8/1994 | Kwak | |
| 5,641,343 A | 6/1997 | Frey | |
| 5,753,000 A | 5/1998 | Chiu et al. | |
| 5,837,020 A | 11/1998 | Cartellone | |
| 6,053,968 A | 4/2000 | Miller | |
| 6,494,940 B1 | 12/2002 | Hak | |
| 6,680,028 B1 | 1/2004 | Harris | |
| 6,955,708 B1 | 10/2005 | Julos et al. | |
| 8,212,146 B1 | 7/2012 | Moore | |
| 9,821,259 B2 | 11/2017 | Bae et al. | |
| 9,943,794 B2 | 4/2018 | Jung | |
| 9,950,289 B2 | 4/2018 | Jung et al. | |
| 10,323,855 B2 * | 6/2019 | Jung | F24F 11/89 |
| 2002/0157415 A1 | 10/2002 | Liu | |
| 2004/0144249 A1 | 7/2004 | Kang et al. | |
| 2005/0066634 A1 | 3/2005 | Genn et al. | |
| 2006/0107834 A1 | 5/2006 | Vandenbelt et al. | |
| 2006/0201119 A1 | 9/2006 | Song | |
| 2006/0277875 A1 | 12/2006 | Schuld | |
| 2007/0137489 A1 | 6/2007 | Luo | |
| 2007/0221061 A1 | 9/2007 | Steiner et al. | |
| 2008/0036411 A1 | 2/2008 | Kiern et al. | |
| 2008/0286163 A1 | 11/2008 | Garfield et al. | |
| 2010/0064895 A1 | 3/2010 | Thurin et al. | |
| 2010/0225012 A1 | 9/2010 | Fitton et al. | |
| 2010/0225015 A1 | 9/2010 | Techlin et al. | |
| 2011/0033346 A1 | 2/2011 | Bohlen | |
| 2011/0308210 A1 | 12/2011 | Crabtree et al. | |
| 2013/0055692 A1 | 3/2013 | Cecchi et al. | |
| 2013/0090052 A1 | 4/2013 | Akhtar | |
| 2014/0020561 A1 * | 1/2014 | Aery | B01D 46/0021 96/224 |
| 2014/0102664 A1 | 4/2014 | Kim et al. | |
| 2014/0216251 A1 | 8/2014 | Jun et al. | |
| 2014/0216259 A1 | 8/2014 | Iwaki | |
| 2015/0306533 A1 | 10/2015 | Matlin et al. | |
| 2015/0345816 A1 | 12/2015 | Donovan | |
| 2016/0032942 A1 | 2/2016 | Jung et al. | |
| 2016/0184753 A1 | 6/2016 | Chu et al. | |
| 2016/0195428 A1 | 7/2016 | McRae | |

FOREIGN PATENT DOCUMENTS

| | | |
|---|---|---|
| CN | 1598413 | 3/2005 |
| CN | 1619229 | 5/2005 |
| CN | 1752617 | 3/2006 |
| CN | 2769724 | 4/2006 |
| CN | 1784258 | 6/2006 |
| CN | 101021345 | 8/2007 |
| CN | 101105307 | 1/2008 |
| CN | 201106913 | 8/2008 |
| CN | 201482362 | 5/2010 |
| CN | 102563752 | 7/2012 |
| CN | 102661295 | 9/2012 |
| CN | 102748817 | 10/2012 |
| CN | 202568987 | 12/2012 |
| CN | 103574770 | 2/2014 |
| CN | 103673076 | 3/2014 |
| CN | 103712318 | 4/2014 |
| CN | 103727632 | 4/2014 |
| CN | 203518040 | 4/2014 |
| CN | 103930730 | 7/2014 |
| CN | 103982994 | 8/2014 |
| CN | 203893332 | 10/2014 |
| CN | 203964288 | 11/2014 |
| CN | 204084651 | 1/2015 |
| CN | 104329785 | 2/2015 |
| CN | 204141826 | 2/2015 |
| CN | 104406235 | 3/2015 |
| CN | 104456772 | 3/2015 |
| CN | 104603545 | 5/2015 |
| CN | 204329221 | 5/2015 |
| CN | 204447560 | 7/2015 |
| CN | 104937359 | 9/2015 |
| CN | 104971567 | 10/2015 |
| CN | 104990155 | 10/2015 |
| CN | 105091106 | 11/2015 |
| CN | 105185242 | 12/2015 |
| CN | 105221452 | 1/2016 |
| CN | 204933080 | 1/2016 |
| CN | 204963008 | 1/2016 |
| CN | 105299862 | 2/2016 |
| CN | 105299863 | 2/2016 |
| CN | 105333499 | 2/2016 |
| CN | 105333528 | 2/2016 |
| CN | 206300285 | 7/2017 |
| CN | 206300287 | 7/2017 |
| CN | 206300288 | 7/2017 |
| CN | 206338921 | 7/2017 |
| DE | 9312051 | 10/1993 |
| EP | 1 950 500 | 7/2008 |
| EP | 2 072 920 | 6/2009 |
| EP | 2 476 968 | 7/2012 |
| EP | 2 837 897 | 2/2015 |
| EP | 2 853 835 | 4/2015 |
| GB | 995962 | 6/1965 |
| GB | 996962 | 6/1965 |
| GB | 2 345 005 | 6/2000 |
| GB | 2516058 | 1/2015 |
| JP | 04-008973 | 3/1992 |
| JP | H04-103549 | 9/1992 |
| JP | H 06-50180 | 6/1994 |
| JP | 7-208779 | 8/1995 |
| JP | 2000-354724 | 12/2000 |
| JP | 2006-022977 | 1/2006 |
| JP | 2007-105578 | 4/2007 |
| JP | 4526372 | 8/2010 |
| JP | 2012-120720 | 6/2012 |
| JP | 2013-217580 | 10/2013 |
| JP | 2014-507277 | 3/2014 |
| JP | 2014-119224 | 6/2014 |
| JP | 2015-080737 | 4/2015 |
| JP | 2015-108497 | 6/2015 |
| JP | 5740503 | 6/2015 |

(56) References Cited

FOREIGN PATENT DOCUMENTS

| | | |
|---|---|---|
| JP | 2015-120138 | 7/2015 |
| JP | 5800652 | 10/2015 |
| JP | 2016-034602 | 3/2016 |
| KR | 20-1993-0002444 | 5/1993 |
| KR | 10-0139487 | 6/1998 |
| KR | 20-0173274 | 3/2000 |
| KR | 20-0289687 | 9/2002 |
| KR | 20-0342073 | 2/2004 |
| KR | 10-2004-0056151 | 6/2004 |
| KR | 10-2004-0108462 | 12/2004 |
| KR | 10-0508312 | 8/2005 |
| KR | 10-2005-0110233 | 11/2005 |
| KR | 10-2005-0115343 | 12/2005 |
| KR | 10-2006-0023457 | 3/2006 |
| KR | 10-2006-0026319 | 3/2006 |
| KR | 10-0674271 | 1/2007 |
| KR | 20-2008-0001777 | 6/2008 |
| KR | 10-2009-0058446 | 6/2009 |
| KR | 10-2009-0087652 | 8/2009 |
| KR | 10-2010-0056797 | 5/2010 |
| KR | 10-2010-0062121 | 6/2010 |
| KR | 10-2010-0070069 | 6/2010 |
| KR | 10-2010-0102507 | 9/2010 |
| KR | 10-2011-0029870 | 3/2011 |
| KR | 10-2012-0060279 | 6/2012 |
| KR | 10-2012-0071992 | 7/2012 |
| KR | 10-1168738 | 7/2012 |
| KR | 10-1203570 | 11/2012 |
| KR | 10-2012-0136137 | 12/2012 |
| KR | 10-2013-0036447 | 4/2013 |
| KR | 10-1278334 | 6/2013 |
| KR | 10-1342606 | 12/2013 |
| KR | 10-2014-0039703 | 4/2014 |
| KR | 10-1385290 | 4/2014 |
| KR | 10-2014-0092953 | 7/2014 |
| KR | 10-2014-0094414 | 7/2014 |
| KR | 10-2014-0096971 | 8/2014 |
| KR | 10-2015-0005594 | 1/2015 |
| KR | 10-1500501 | 3/2015 |
| KR | 10-1506653 | 3/2015 |
| KR | 10-1512664 | 4/2015 |
| KR | 10-1516365 | 5/2015 |
| KR | 10-2016-0012796 | 2/2016 |
| KR | 10-2016-0015084 | 2/2016 |
| KR | 10-2016-0017587 | 2/2016 |
| KR | 10-2016-0028292 | 3/2016 |
| KR | 10-1599634 | 3/2016 |
| KR | 10-2016-0048499 | 5/2016 |
| KR | 10-2016-0053649 | 5/2016 |
| KR | 10-2016-0104837 | 9/2016 |
| WO | WO 2010/109944 | 9/2010 |
| WO | WO 2013/121672 | 8/2013 |
| WO | WO 2015/171571 | 11/2015 |

OTHER PUBLICATIONS

U.S. Appl. No. 15/363,587, filed Nov. 29, 2016.
U.S. Appl. No. 15/659,989, filed Jul. 26, 2017.
U.S. Appl. No. 16/409,017, filed May 10, 2019.
U.S. Appl. No. 15/660,105, filed Jul. 26, 2017.
U.S. Appl. No. 15/660,122, filed Jul. 26, 2017.
U.S. Appl. No. 15/363,643, filed Nov. 29, 2016.
U.S. Office Action issued in U.S. Appl. No. 15/660,462 dated Jul. 19, 2019.
U.S. Office Action issued in U.S. Appl. No. 15/660,207 dated Jul. 22, 2019.
United States Office Action dated Dec. 4, 2019 issued in co-pending related U.S. Appl. No. 15/660,462.
United States Office Action dated Dec. 6, 2019 issued in co-pending related U.S. Appl. No. 16/548,045.
U.S. Appl. No. 15/926,129, filed Mar. 20, 2018.
U.S. Appl. No. 15/659,869, filed Jul. 26, 2017.
U.S. Appl. No. 15/659,878, filed Jul. 26, 2017.
U.S. Appl. No. 16/527,140, filed Jul. 31, 2019.
U.S. Appl. No. 16/687,941, filed Nov. 19, 2019.
U.S. Appl. No. 15/660,076, filed Jul. 26, 2017.
U.S. Appl. No. 15/660,207, filed Jul. 26, 2017.
U.S. Appl. No. 15/660,287, filed Jul. 26, 2017.
U.S. Appl. No. 15/660,362, filed Jul. 26, 2017.
U.S. Appl. No. 15/660,462, filed Jul. 26, 2017.
U.S. Appl. No. 16/548,045, filed Aug. 22, 2019.
Chinese Office Action dated Mar. 5, 2019 issued in Application No. 201611089126.6 (with English Translation).
Chinese Office Action dated Mar. 27, 2019 issued in Application No. 201611089196.1 (with English Translation).
Korean Office Action dated May 2, 2019 issued in Application No. 10-2019-0025204.
Chinese Office Action dated Feb. 28, 2019 issued in Application No. 201611087595.4 (with English Translation).
Chinese Office Action dated Feb. 28, 2019 issued in Application No. 201611089358.1 (with English Translation).
Korean Office Action dated Jul. 22, 2019 issued in KR Application No. 10-2019-0060135.
Chinese Office Action dated Jun. 10, 2019 issued in Application No. 201710660027.7.
Chinese Office Action dated Jul. 29, 2019 issued in Application No. 201710659929.9.
Chinese Office Action dated May 27, 2019 issued in Application No. 201710637948.1.
Chinese Office Action dated Jun. 4, 2019 issued in Application No. 201710638173.X.
Chinese Office Action dated Jun. 24, 2019 issued in Application No. 201710637920.8.
Chinese Office Action dated Jun. 26, 2019 issued in Application No. 201710790121.4.
Chinese Office Action dated Jun. 27, 2019 issued in Application No. 201710637967.4.
Korean Notice of Allowance dated Jul. 1, 2019 issued in Application No. 10-2019-0063475.
Chinese Office Action dated Jul. 16, 2019 issued in Application No. 201710638026.2.
United States Office Action dated Aug. 16, 2019 issued in co-pending related U.S. Appl. No. 15/660,287.
United States Office Action dated Aug. 22, 2019 issued in co-pending related U.S. Appl. No. 15/926,129.
United States Office Action dated Jan. 20, 2017 issued in U.S. Appl. No. 15/364,369.
United States Office Action dated Jan. 20, 2017 issued in U.S. Appl. No. 15/363,156.
United States Office Action dated Jan. 23, 2017 issued in U.S. Appl. No. 15/364,410.
United States Office Action dated Jan. 23, 2017 issued in U.S. Appl. No. 15/363,204.
United States Office Action dated Jan. 23, 2017 issued in U.S. Appl. No. 15/364,467.
United States Office Action dated Feb. 10, 2017 issued in U.S. Appl. No. 15/363,111.
Korean Office Action dated Jan. 26, 2017 issued in Application No. 10-2016-0073055.
Korean Office Action dated Jan. 26, 2017 issued in Application No. 10-2016-0073083.
Korean Office Action dated Jan. 26, 2017 issued in Application No. 10-2016-0077888.
International Search Report dated Mar. 20, 2017 issued in Application No. PCT/KR2016/013906.
International Search Report dated Mar. 21, 2017 issued in Application No. PCT/KR2016/013907.
International Search Report dated Mar. 30, 2017 issued in Application No. PCT/KR2016/013912.
International Search Report dated Mar. 30, 2017 issued in Application No. PCT/KR2016/013908.
Korean Office Action dated Apr. 20, 2017 issued in Application No. 10-2016-0132790.
European Search Report dated Apr. 25, 2017 issued in Application No. 16201086.2-1602.

(56) References Cited

OTHER PUBLICATIONS

European Search Report dated Apr. 25, 2017 issued in Application No. 17157045.0-1602.
European Search Report dated Jun. 21, 2017 issued in Application No. 16201095.3.
European Search Report dated Jun. 21, 2017 issued in Application No. 16201093.8.
Korean Office Action dated Jun. 21, 2017 issued in Application No. 10-2017-0056789.
Korean Office Action dated Jun. 21, 2017 issued in Application No. 10-2017-0056790.
Korean Office Action dated Jun. 21, 2017 issued in Application No. 10-2017-0056791.
Korean Office Action dated Jun. 21, 2017 (10-2017-0056865).
Korean Office Action dated Jun. 21, 2017 (10-2017-0056885).
Korean Office Action dated Jun. 21, 2017 (10-2017-0056886).
European Search Report dated Jun. 23, 2017 issued in Application No. 16201089.6.
European Search Report dated Jun. 23, 2017 issued in Application No. 16201088.8.
Korean Office Action dated Jun. 30, 2017 issued in Application No. 10-2017-0056864.
European Search Report dated Jul. 14, 2017 issued in Application No. 16201094.6.
U.S. Office Action issued in U.S. Appl. No. 15/364,369 dated Jul. 14, 2017.
European Search Report dated Jul. 14, 2017 issued in Application No. 16201092.0.
European Search Report dated Jul. 20, 2017 issued in Application No. 16201090.4.
European Search Report dated Jul. 20, 2017 issued in Application No. 16201091.2.
Korean Notice of Allowance dated Aug. 15, 2017 issued in Application No. 10-2016-0074369.
Korean Office Action dated Aug. 22, 2017 issued in Application No. 10-2016-0073055.
Korean Office Action dated Aug. 31, 2017 issued in Application No. 10-2016-0073063.
Korean Office Action dated Aug. 31, 2017 issued in Application No. 10-2016-0073090.
Korean Office Action dated Oct. 31, 2017.
European Search Report dated Jan. 17, 2018.
European Search Report dated Jan. 18, 2018.
Korean Office Action dated Apr. 12, 2018.
Korean Notice of Allowance dated Apr. 17, 2018.
Korean Notice of Allowance dated Jun. 11, 2018.
U.S. Office Action issued in U.S. Appl. No. 15/363,643 dated Oct. 24, 2018.
United States Office Action dated Nov. 8, 2018 issued in co-pending related U.S. Appl. No. 15/363,438.
United States Office Action dated Dec. 3, 2018 issued in co-pending related U.S. Appl. No. 15/363,587.
Chinese Office Action dated Jan. 11, 2019 issued in Application No. 201611089233.9 (with English Translation).
United States Office Action dated Feb. 6, 2019 issued in co-pending related U.S. Appl. No. 15/660,105.
United States Office Action dated Feb. 6, 2019 issued in co-pending related U.S. Appl. No. 15/660,122.
United States Office Action dated Feb. 21, 2019 issued in co-pending related U.S. Appl. No. 15/659,878.
Chinese Office Action dated Feb. 22, 2019 with English Translation.
United States Office Action dated Mar. 1, 2019 issued in co-pending related U.S. Appl. No. 15/363,438.
United States Office Action dated Mar. 5, 2019 issued in co-pending related U.S. Appl. No. 15/363,587.
U.S. Office Action issued in U.S. Appl. No. 15/660,076 dated May 8, 2019.
Japanese Office Action dated Aug. 20, 2019.
Chinese Office Action dated Oct. 25, 2019.

* cited by examiner

Fig. 5
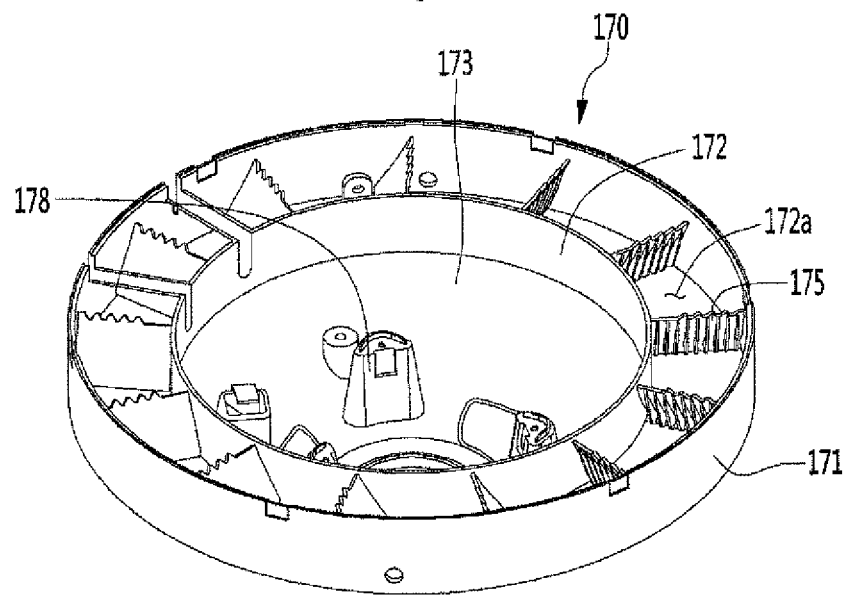
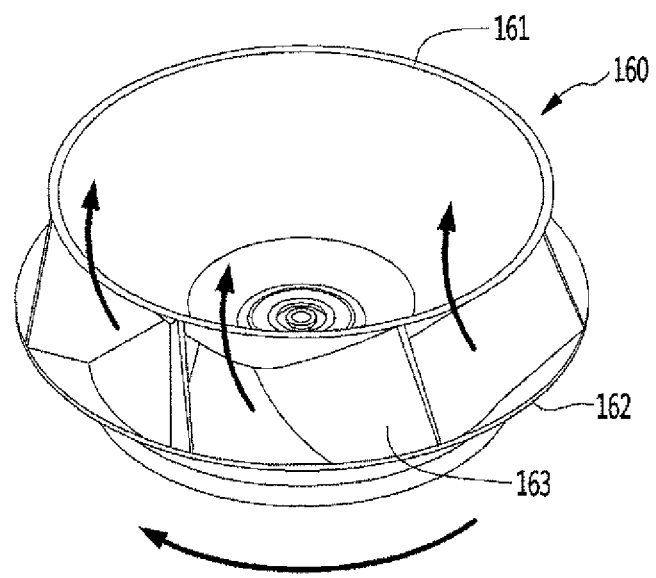

AIR CLEANER

CROSS-REFERENCE TO RELATED APPLICATIONS

This application is a Continuation Application of prior U.S. patent application Ser. No. 15/441,957 filed Feb. 24, 2017, now U.S. Pat. No. 10,323,855, which claims priority under 35 U.S.C. § 119 to Korean Application Nos. 10-2016-0023663 filed in Korea on Feb. 26, 2016, 10-2016-0139376 filed in Korea on Oct. 25, 2016 and 10-2016-0171724 filed on Dec. 15, 2016, whose entire disclosures are hereby incorporated by reference.

BACKGROUND

1. Field

An air cleaner is disclosed herein.

2. Background

An air cleaner is a device that suctions in and purifies contaminated air and then discharges purified air. For example, the air cleaner may include a blower that introduces outside air into the air cleaner and a filter capable of filtering dust and bacteria, for example.

Generally, the air cleaner is configured to purify an indoor space, such as a home or an office. According to the air cleaner in the related art, there is a problem that a capacity thereof is limited, and thus, purification of air in an entire indoor space is limited. Accordingly, air around the air cleaner is purified whereas air in a space away from the air cleaner is not purified.

In order to solve this problem, there are efforts to improve a performance of a fan provided in the air cleaner. However, noise generated by the fan gradually increases as a blowing amount of the fan increases. Accordingly, there is a problem in that reliability of the product is decreased. Finally, there is inconvenience in that the air cleaner has to be moved by a user in order to purify air in the desired space.

A related art air cleaner is disclosed in Korean Publication No. KR 10-2012-0071992, published on Jul. 3, 2012 and entitled "AIR CLEANER", which is hereby incorporated by reference. According to this disclosure, air cleaning components, such as the fan and a filter are installed, in an inside of a case having a substantially rectangular parallelepiped shape of a main body of the air cleaner. Air suction ports are formed on a side portion and a lower portion of the main body of the air cleaner and an air discharge port is formed on an upper portion of the main body thereof.

According to this configuration, there is a problem in that a suction capacity is reduced as the contaminated air is suctioned from a limited direction, that is, from a side direction and a lower direction relative to the air cleaner. A corner portion of the case having a rectangular parallelepiped shape provides structural resistance interfering with the suction of air.

In addition, there is a problem in that an air cleaning function is limited as purified air does not flow to a space away from the air cleaner, whereas air around the air cleaner is purified. That is, the air which is purified in the air cleaner is discharged in only one direction, that is, only in an upward direction. Further, there is a problem in that a blowing capacity is limited as only one blowing fan is provided in the main body of the air cleaner.

BRIEF DESCRIPTION OF THE DRAWINGS

Embodiments will be described in detail with reference to the following drawings in which like reference numerals refer to like elements, and wherein:

FIG. 5 is an exploded perspective view of a first fan and a first guide of the air cleaner of FIG. 1;

DETAILED DESCRIPTION

Figure 1:
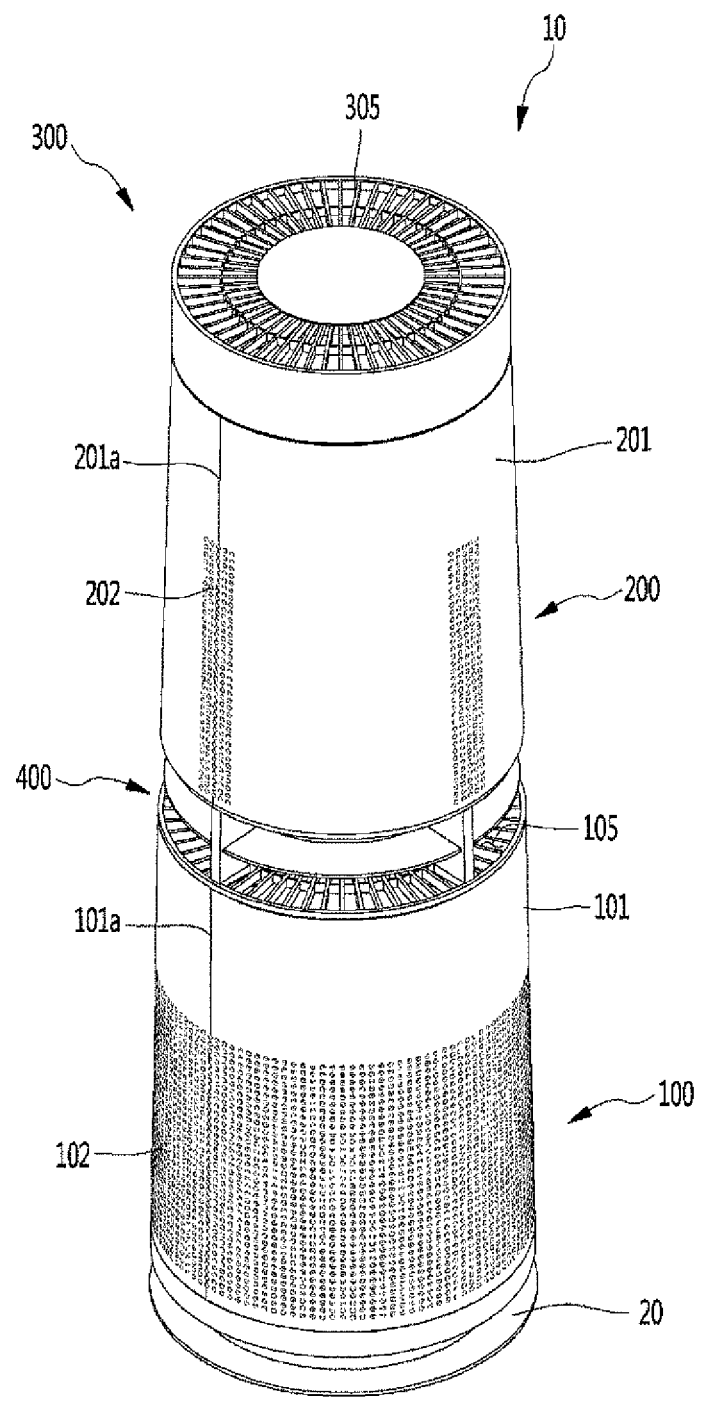
FIG. 1 is a perspective view of an air cleaner according to an embodiment.

Hereinafter, embodiments will be described in detail with reference to the illustrative drawings. Regarding the reference numerals assigned to the components in the drawings, it should be noted that the same components may be designated by the same reference numerals, wherever possible, even though they are shown in different drawings. Also, in the description of embodiments, specific description of known related configuration or functions may be omitted when it is deemed that such description may cause ambiguous interpretation of the present invention.

Also, in the description of embodiments, terms such as first, second, A, B, (a), (b) or the like may be used herein when describing components. Each of these terminologies is not used to define an essence, order or sequence of a corresponding component but used merely to distinguish the corresponding component from other component(s). In a case where it is described that any component is "connected" or "coupled" to another component, the component may be directly or indirectly connected or coupled to another component. However, it is to be understood that another component may be "connected" or "coupled" between the components.

FIG. 1 is a perspective view of an air cleaner according to an embodiment. With reference to FIG. 1, the air cleaner 10 according to this embodiment may include blowing devices or blowers 100 and 200 that generate air flow and a flow adjusting device or adjuster 300 that adjusts a discharge direction of the air flow generated in the blowing devices 100 and 200. The blowing devices 100 and 200 may include a first blowing device 100 that generates a first air flow and a second blowing device 200 that generates a second air flow.

The first blowing device 100 and the second blowing device 200 may be provided in a vertical direction. For example, the second blowing device 200 may be provided on or at an upper side of the first blowing device 100. In this case, the first air flow is a flow of indoor air suctioned from a lower side of the air cleaner 10 and the second air flow is a flow of indoor air suctioned from an upper side of the air cleaner 10.

The air cleaner 10 may include cases 101 and 201 that form an outer appearance thereof. That is, the cases 101 and 201 may include a first case 101 that forms an outer appearance of the first blowing device 100. The first case 101 may have a cylindrical shape. An upper portion of the first case 101 may have a diameter which is less than a diameter of a lower portion thereof. In other words, the first case 101 may have a truncated cone shape.

The first blowing device 100 and the second blowing device 200 may be referred to as a "first air cleaning module or cleaner 100" and a "second air cleaning module or cleaner 200", respectively, in that the first blowing device 100 and the second blowing device 200 perform a function of cleaning air in a space to be cleaned. The first blowing device 100 may be referred to as a "lower air cleaning module or cleaner" or "lower module or cleaner" in that the first blowing device 100 is provided at a lower portion of the air cleaner 10 and the second blowing device 200 may be referred to as an "upper air cleaning module or cleaner" or "upper module or cleaner" in that the second blowing device 200 is provided at an upper portion of the air cleaner 10. The flow adjusting device 300 may be referred to as "flow adjusting module or adjuster 300" or "flow control module 300".

The first case 101 may include a first separation portion 101a at which two parts which constitute the first case 101 may be assembled or disassembled. The first case 101 may further include a hinge portion or hinge which is provided on an opposite of the first separation portion 101a. The two parts may be capable of being relatively rotated about the hinge portion.

When at least any one part of the two parts rotates, the first case 101 may be opened and separated from the air cleaner 10. A locking device or lock may be provided at a portion at which the two parts are coupled, that is, a side opposite to the hinge portion. The locking device may include a locking projection or a magnet or coupler. Components of the first blowing device 100 may be replaced or repaired by opening the first case 101.

The first case 101 may include a first suction portion or inlet 102 through which air may be suctioned in a radial direction. The first suction portion 102 may include one or more through hole formed to pass through at least a portion of the first case 101. A plurality of first suction portions 102 may be provided.

The plurality of first suction portions 102 may be evenly provided in a circumferential direction along an outer circumferential surface of the first case 101 so that air suction may be performed in any direction relative to the first case 101. In other words, air may be suctioned in 360 degree directions relative to a center line that extends in the vertical direction and passes through an inside center of the first case 101.

Accordingly, a suction amount of air may be increased by the first case 101 having a cylindrical shape and the plurality of first suction portions 102 formed along the outer circumferential surface of the first case 101. Flow resistance to suctioned air may be reduced by avoiding a cube shape having edges or edge portions such as the case of the related art air cleaner.

Air which is suctioned in through the first suction portion 102 may flow substantially in the radial direction from the outer circumferential surface of the first case 101. Directions may be defined as follows. Referring to the FIG. 1, the vertical direction may refer to an axial direction and a transverse direction may refer to the radial direction. The axial direction may correspond to a central axis direction of the first fan 160 and the second fan 260, which are described hereinafter, that is, a motor shaft direction of the fan. The radial direction may refer to a direction which is perpendicular to the axial direction. The circumferential direction may refer to a virtual circle direction which is formed when rotating about the axial direction and having a distance of the radial direction as a rotational radius.

The first blowing device 100 may include a base 20 provided at a lower side of the first case 101 and placed on the ground. The base 20 may be positioned spaced apart from a lower end portion or end of the first case 101 in a downward direction. A base suction portion or inlet 103 may be formed in a space between the first case 101 and the base 20.

Air which is suctioned in through the base suction portion 103 may flow in an upward direction through a suction port 112 of a suction grill 110 (see FIG. 2), which may be provided in or at an upper side of the base 20. In other words, the first blowing device 100 may include the plurality of suction portions 102 and the base suction portion 103. Air in a lower portion of the indoor space may be easily introduced to the first blowing device 100 through the plurality of suction portions 102 and the base suction portion 103. Accordingly, the suction amount of air may be increased.

A first discharge portion or outlet 105 may be formed at an upper portion of the first blowing device 100. The first discharge portion 105 may be formed on a first discharge grill 195 of a first discharge guide device or guide 190 (see, FIG. 8) which may be provided in the first blowing device 100. The first discharge guide 190 may form an outer appearance of an upper end portion or end of the first blowing device 100. Air discharged through the first discharge portion 105 may flow to the upper side in the axial direction.

The cases 101 and 201 may include a second case 201 which may form an outer appearance of the second blowing device 200. The second case 201 may have a cylindrical shape. An upper portion of the second case 201 may have a diameter which is less than a diameter of a lower portion thereof. In other words, the second case 201 may have a truncated cone shape.

The second case 201 may include two parts and a hinge portion or hinge which are capable of being assembled or being disassembled through a second separation portion 201*a*. The second case 201 may be openable similar to the first case 101. The second case 201 may be the same or similar to the first case 101, and thus, repetitive disclosure has been omitted. Inner components of the second blowing device 200 may be replaced or repaired by opening the second case 201.

A diameter of a lower end portion or end of the second case 201 may be less than a diameter of an upper end portion or end of the first case 101. Accordingly, in a general shape of the cases 101 and 201, a lower cross-sectional area of the cases 101 and 102 may be formed to be greater than an upper cross-sectional area. Accordingly, the air cleaner 10 may be stably supported on the ground.

The second case 201 may include a second suction portion or inlet 202 through which air may be suctioned in the radial direction. The second suction portion 202 may include one or more through hole formed to pass through at least a portion of the second case 201. A plurality of the second suction portion 202 may be provided.

The plurality of second suction portions 202 may be evenly provided in the circumferential direction along an outer circumferential surface of the second case 201 so that air suction may be performed in any direction relative to the second case 201. In other words, air may be suctioned in 360 degree directions relative to a center line that extends in the vertical direction and passes through an inside center of the second case 201.

Accordingly, a suction amount of air may be increased by the second case 201 having a cylindrical shape and the plurality of second suction portions 202 formed along the outer circumferential surface of the second case 201. Flow resistance to suctioned air may be reduced by avoiding a cube shape having an edge portions such as the case of the related art air cleaner. Air which is suctioned in through the second suction portion 202 may flow substantially in the radial direction from the outer circumferential surface of the second case 201.

The air cleaner 10 may include a dividing device or divider 400 provided between the first blowing device 100 and the second blowing device 200. By the dividing device 400, the second blowing device 200 may be positioned at the upper side of the first blowing device 100 spaced apart therefrom. The dividing device 400 will be described hereinafter, with reference to the drawings.

The flow adjusting device 300 may be provided at an upper side of the second blowing device 100. An air flow path of the second blowing device 100 may communicate with an air flow path of the flow adjusting device 300. The air passing through the second blowing device 100 may be discharged through a second discharge portion or outlet 305 to the outside via the air flow path of the flow adjusting device 300. The second discharge portion 305 may be provided on or at an upper end portion of the flow adjusting device 300.

Figure 19:
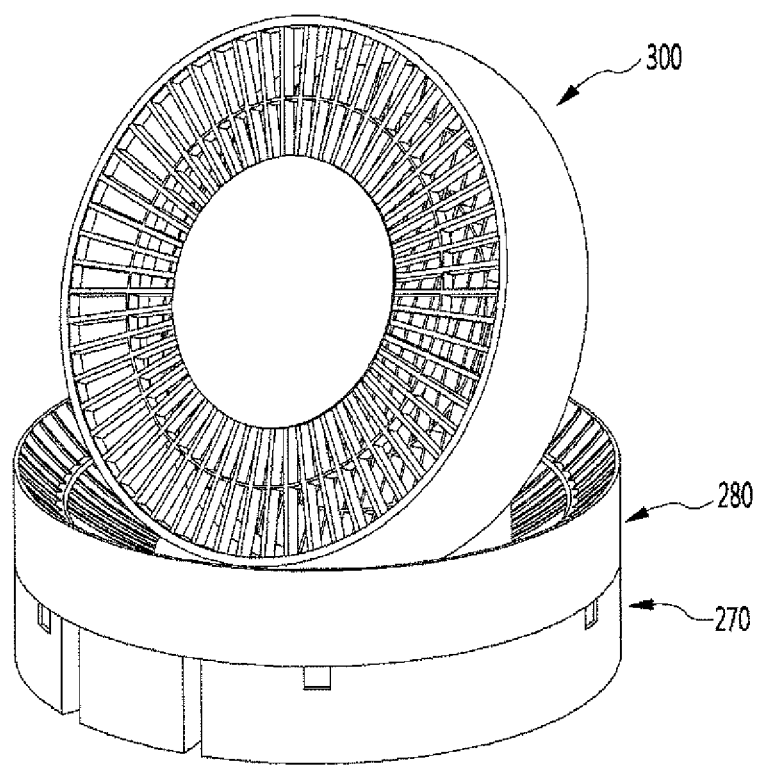
FIG. 19 to FIG. 21 are views illustrating a state in which the flow adjusting device of FIG. 12 is in a second position.
Figure 20:
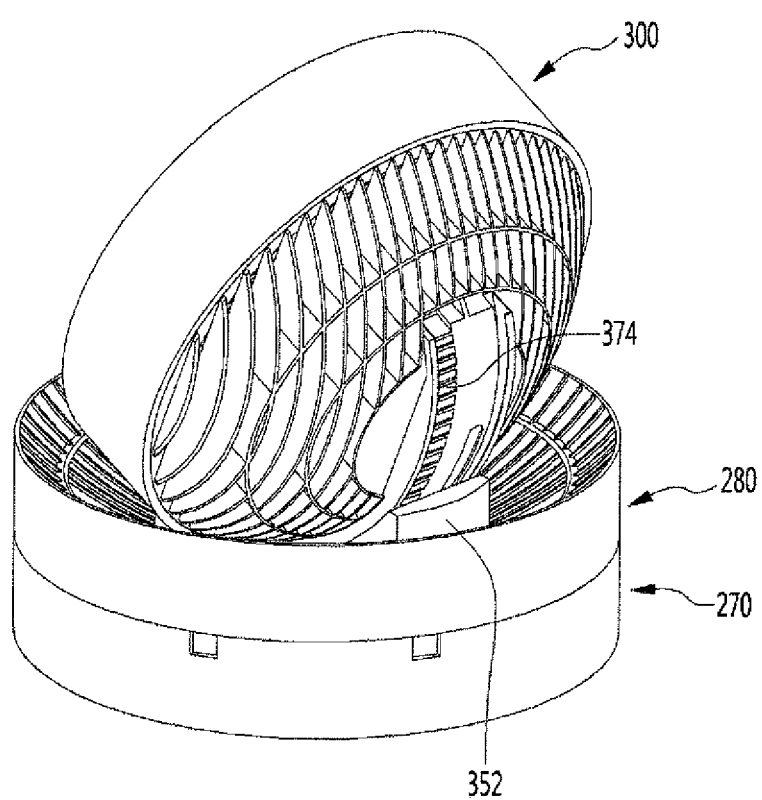
Figure 21:
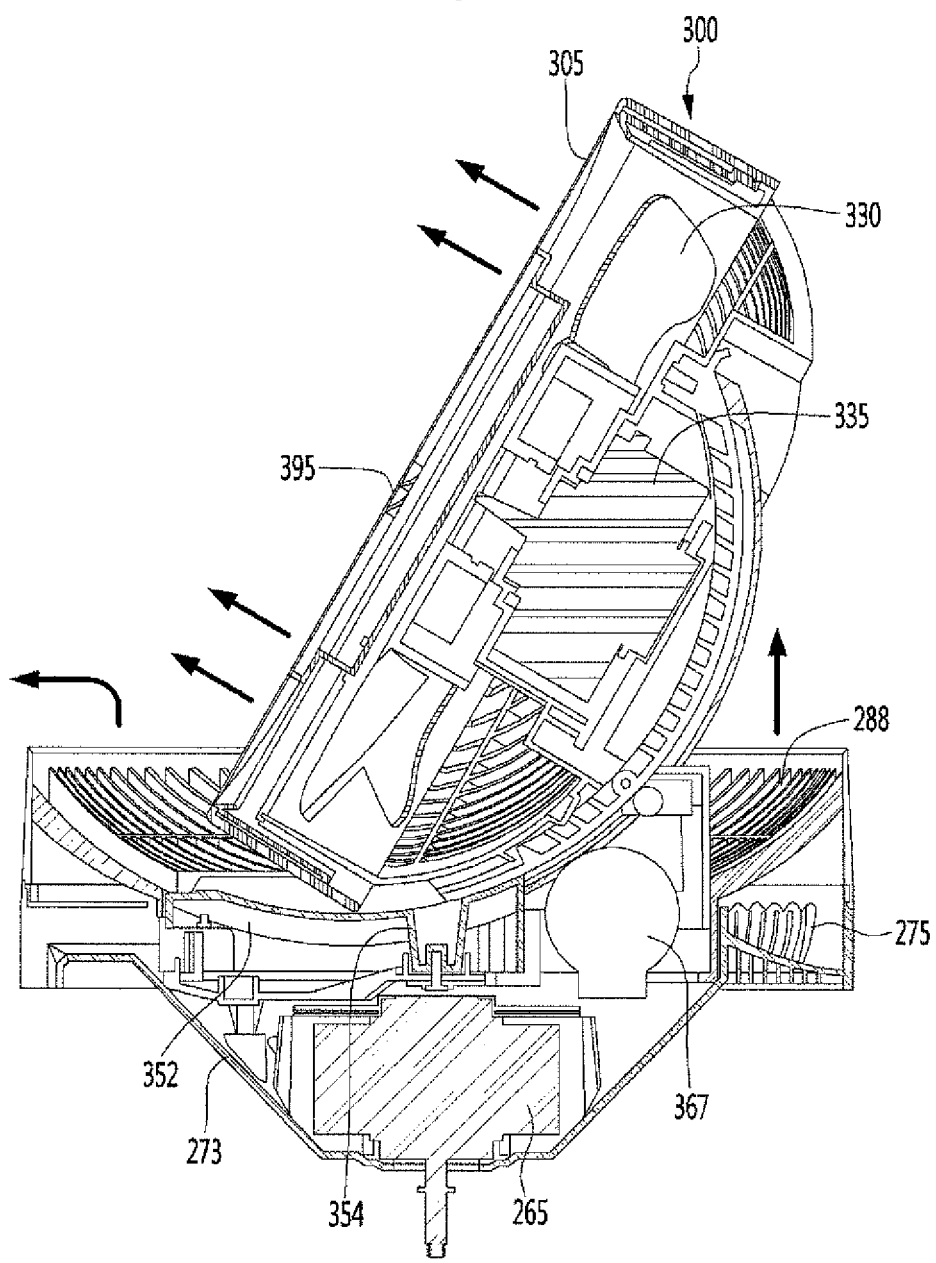

The flow adjusting device 300 may be movable. That is, the flow adjusting device 300 may be movable between a laid out state (first position), as illustrated in FIG. 1, or an inclined state (second position), as illustrated in FIG. 19 to FIG. 21.

Figure 2:
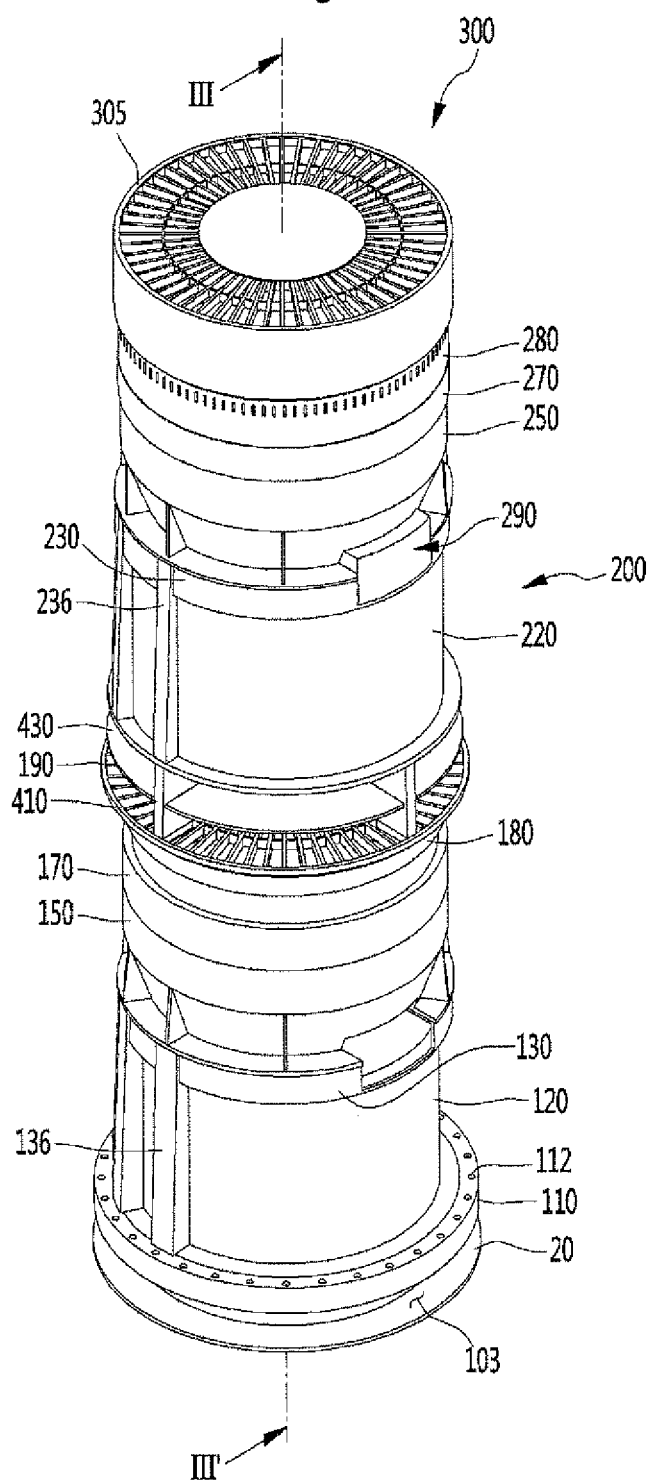
FIG. 2 is a perspective view illustrating an internal configuration of the air cleaner of FIG. 1.
Figure 3:
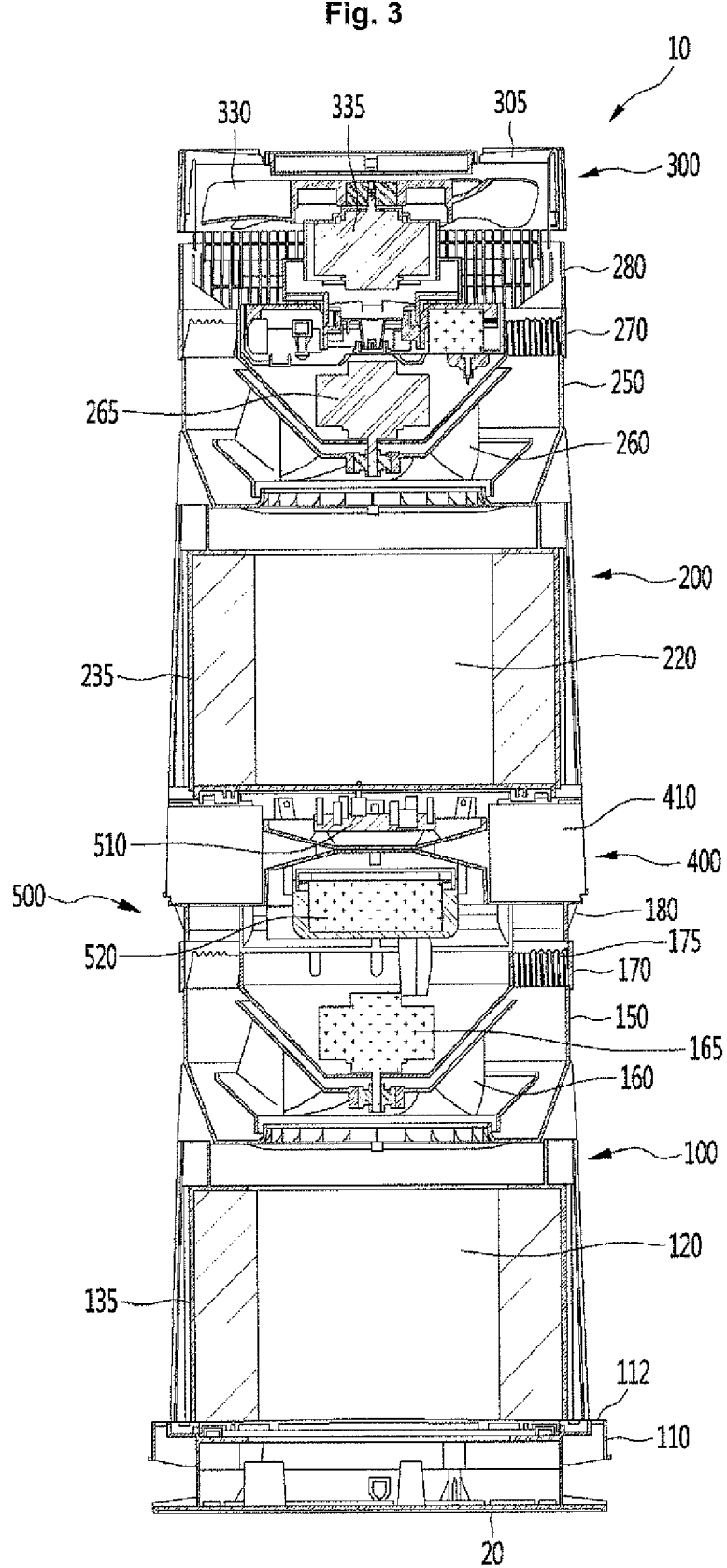
FIG. 3 is a cross-sectional view, taken along line in FIG. 2.
Figure 4:
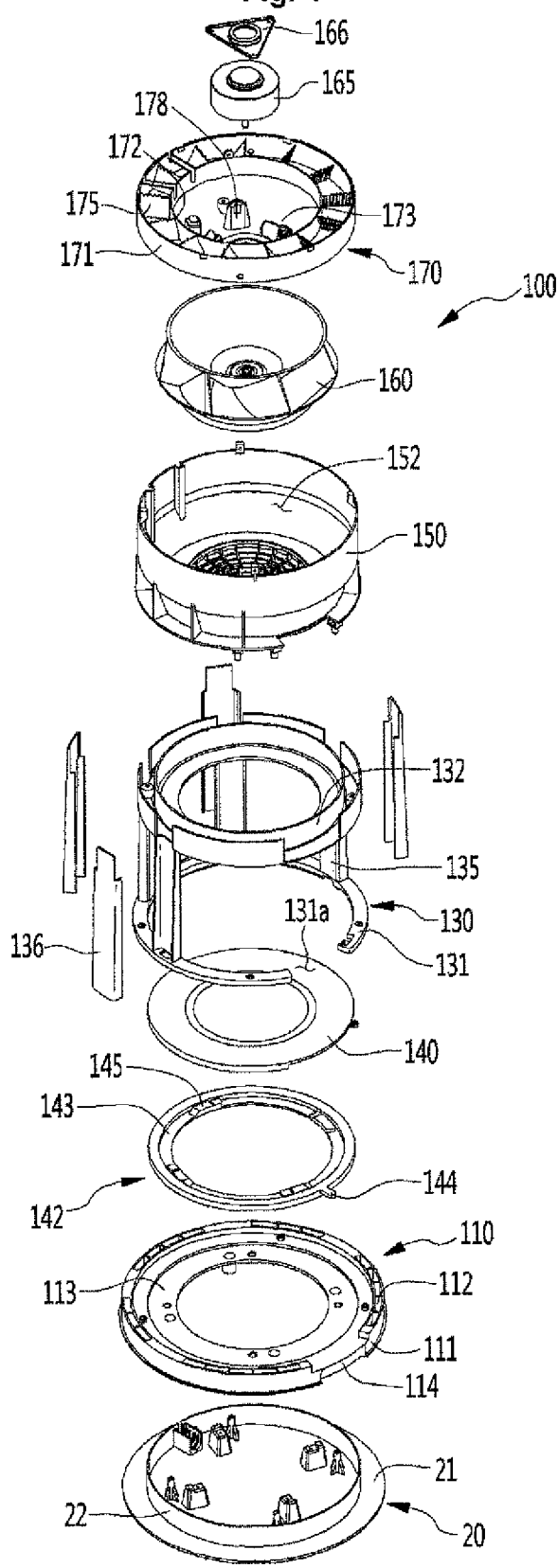
FIG. 4 is an exploded perspective view of a first blowing device of the air cleaner of FIG. 1.
Figure 6:
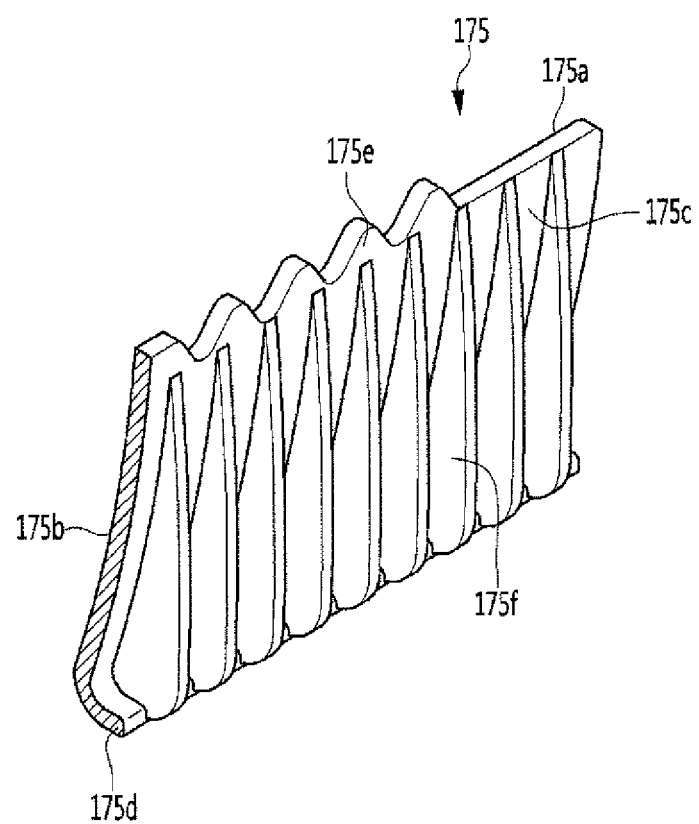
FIG. 6 is a perspective view of a guide rib of the air cleaner of FIG. 1.
Figure 7:
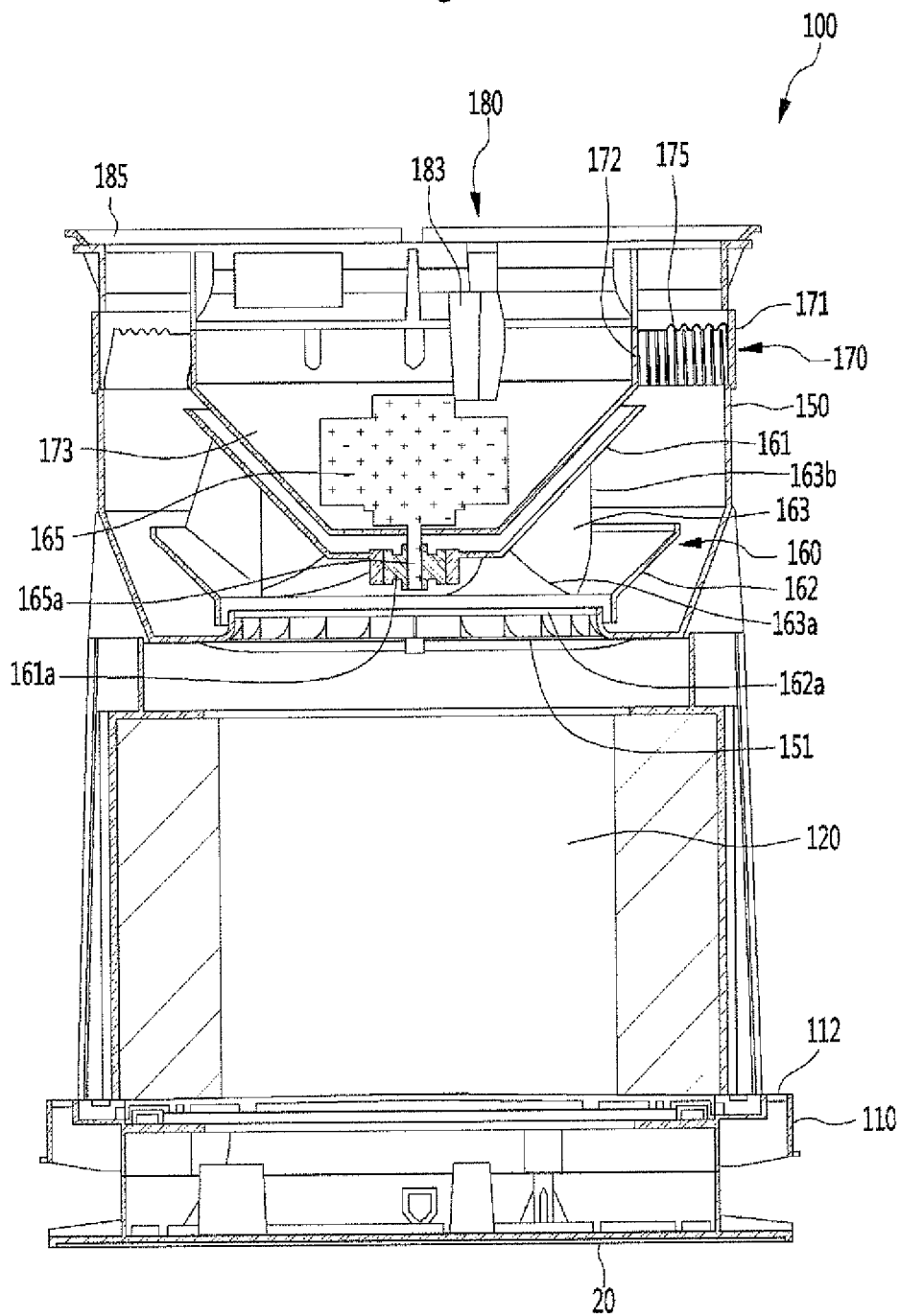
FIG. 7 is a cross-sectional view of a portion of the first blowing device of the air cleaner of FIG. 1.

FIG. 2 is a perspective view illustrating an internal configuration of the air cleaner of FIG. 1. FIG. 3 is a cross-sectional view, taken along line in FIG. 2. FIG. 4 is an exploded perspective view of a first blowing device of the air cleaner of FIG. 1. FIG. 5 is an exploded perspective view of a first fan and a first guide of the air cleaner of FIG. 1. FIG. 6 is a perspective view of a guide rib of the air cleaner of FIG. 1. FIG. 7 is a cross-sectional view of a portion of the first blowing device of the air cleaner of FIG. 1.

With reference to FIG. 2 to FIG. 4, the base 20 and the suction grill 110 which may be provided on or at the upper side of the base 20 may be included in the first blowing device 100 according to this embodiment. The base 20 may include a base main body 21 which may be placed on the ground and a base projecting portion or projection 22 that projects from the base main body 21 in the upward direction and on which the suction grill 110 may be placed.

The base main body 21 and the suction grill 110 may be spaced apart from each other by the base projecting portion 22. The base suction portion 103 which forms a suction space of air may be included between the base 20 and the suction grill 110. The suction grill 110 may include a grill main body 111 having a substantially ring shape and the suction port 112 which may be formed or provided on or at a rim portion or rim of the grill main body 111. A plurality of the suction ports 112 may be provided spaced apart from each other along the rim portion. The plurality of suction ports 112 may communicate with the base suction portion 103.

The air which may be suctioned in through the suction port 112 and the base suction portion 103 may pass through a first filter member or filter 120. In other words, air may be introduced to an inside portion or inside of the first filter 120 having a cylindrical shape through an outer circumferential surface thereof. That is, the first filter 120 may have a cylindrical shape and a filter surface that filters air.

The suction grill 110 may include a lever supporting portion or support 113 that forms an upper surface of the grill main body 111 and supports a lever device or lever 142 and a groove portion or groove 114 depressed from an outer circumferential surface in a radial or inward direction of the grill main body 111. The groove portion 113 may provide a space in which a handle 144 described hereinafter is capable of moving.

The first blowing device 100 may include the lever device 142 which may be provided on or at an upper side of the suction grill 110 and which may be operable by a user. The lever device 142 may include a lever main body 143 which may have a substantially ring shape and be rotatable.

The lever main body 143 may include one or more lever projecting portion or projection 145 which may be provided on or at a rim portion or rim of the lever main body 143. The lever projecting portion 145 may project in the upward direction from an upper surface of the rim portion of the lever main body 143. A plurality of the lever projecting portions 145 may be provided and may have an inclined surface in order to move a supporting device or support 140 described hereinafter in the upward or downward direction.

The handle 144 may be provided in or at an outer circumferential surface of the lever main body 143. A user may grasp the handle 144 and then rotate the lever main body 143 in a clockwise direction or in a counterclockwise direction.

The supporting device 140, which supports the first filter member 120, may be provided on or at an upper side of the lever device 142. The lever device 142 may support a lower surface of the supporting device 140. The supporting device

140 may include a support projecting portion or projection (not illustrated) which may be in contact with the lever projecting portion 145. The support projecting portion may project from the lower surface of the supporting device 140 in the downward direction and a plurality of support projecting portions may be provided corresponding to a number of the lever projecting portion 145. The support projecting portion may include an inclined surface.

The lever projecting portion 145 may be rotated along with the lever main body 143 when the lever main body 143 is rotated. When an upper portion of the lever projecting portion 145 is in contact with a lower portion of the support projecting portion, the lever main body 143 may push the supporting device 140 in the upward direction. When the supporting device 140 moves in the upward direction, the first filter 120 is in a state of being coupled to the first blowing device 100.

On the other hand, when the lower portion of the lever projecting portion 145 is in contact with the upper portion of the support projecting portion, the supporting device 140 may move downwardly. When the supporting device 140 moves in the downward direction, the first filter 120 may be in a state (released state) of being separated from the first blowing device 100.

The first blowing device 100 may further include a first filter frame 130 which forms a mounting space of the first filter 120. That is, the first filter frame 130 may include a first frame 131 which forms a lower portion of the first filter frame 130 and a second frame 132 which forms an upper portion of the first filter frame 130.

The first frame 131 may have a substantially ring shape, a portion of which may be cutout. An inner space having a ring shape of the first frame 131 may form at least a portion of the air flow path that passes through the first filter frame 130.

The lever device 142 and the supporting device 140 may be positioned in or at an inner circumferential surface side of the first frame 131. A seating surface, on which the first filter member 120 may be placed, may be included in the upper surface of the supporting device 140. A handle space portion or space 131a, in which the handle 144 of the lever device 142 may be operated, may be defined by a cut portion of the first frame 131. The handle 144 may be positioned on or in the handle space portion 131a, and thus, may be operated in the clockwise direction or in the counterclockwise direction.

The second frame 132 may be positioned spaced apart from the first frame 131 in the upward direction. The second frame 132 may have a substantially ring shape. An inner space having a ring shape of the second frame 132 may form at least a portion of the air flow path that passes through the first filter frame 130. The upper portion of the second frame 132 may support a first fan housing 150 described hereinafter.

The first filter frame 130 may further include a first filter supporting portion or support 135 which extends from the first frame 131 to the second frame 132 in the upward direction. The first frame 131 and the second frame 132 may be spaced apart from each other by the first filter supporting portion 135. A plurality of first filter supporting portions 135 may be provided and the plurality of the first filter supporting portions 135 may be arranged in the circumferential direction, and thus, may be connected to rim portions of the first frame 131 and the second frame 132.

A mounting space of the first filter 120 may be defined by the plurality of first filter supporting portions 135 and the first frame 131 and the second frame 132. The first filter 120 may be detachably mounted on or in the mounting space. The first filter 120 may have a cylindrical shape and air may be introduced through an outer circumferential surface of the first filter 120. Impurities, such as fine dust in air, may be filtered when passing through the first filter 120.

The air may be introduced from any direction to the first filter 120 having the cylindrical shape. Accordingly, a filtering area of air may be increased.

The mounting space may have a cylindrical shape corresponding to a shape of the first filter 120. The first filter 120 may be slidably introduced toward the mounting space in a mounting process. In contrast, the first filter 120 may be slidably withdrawn from the mounting space in a separating process.

That is, when the handle 144 is operated in a state in which the first filter 120 is located on the upper surface of the supporting device 140, the first filter 120 may be put into a released position with the first filter 120 being moved in the downward direction. The first filter 120 may be slid to the outside in the radial direction and may be separated from the mounting space.

In contrast, in a state of being separated from the mounting space, the first filter 120 may be slid toward the mounting space to the inside in the radial direction, may be supported on the upper surface of the supporting device 140, and thus, may be put in close contact upwardly by operation of the handle 144. At this time, the first filter 120 may be in a coupling position. A first supporting portion cover 136 may be coupled with an outside of the first filter supporting portion 135.

The first blowing device 100 may further include the first fan housing 150, which may be provided on or at an outlet side of the first filter 120. A first fan 160 may be accommodated in an inner space 152 of the first fan housing 150. The first fan housing 150 may be supported by the first filter frame 130.

A first fan introducing portion 151 which guides introduction of air to an inside portion or inside of the first fan housing 150 may be included in a lower portion of the first fan housing 150. This may prevent a finger, for example, of a user from being inserted into the first fan housing 150 when the first filter 120 is separated from the first filter frame 130.

The first fan 160 may be placed on or at an upper side of the first fan introducing portion 151. For example, the first fan 160 may include a centrifugal fan which introduces air in the axial direction and then discharges air to an upper side in the radial direction. That is, the first fan 160 may include a hub 161 to which a rotational shaft 165a of a first fan motor 165, which may be a centrifugal fan motor, may be coupled, a shroud 162 which may be disposed or provided in a state of being spaced apart from the hub 161, and a plurality of blades 163, which may be disposed or provided between the hub 161 and the shroud 162. The first fan motor 165 may be coupled to the upper side of the first fan 160.

The hub 161 may have a bowl shape, a diameter of which may be gradually reduced in the downward direction. The hub 161 may include a shaft coupling portion to which the rotational shaft 165a may be coupled and a first blade coupling portion that extends at an incline from the shaft coupling portion in the upward direction. The shroud 162 may include a lower end portion or lower end, on or at which a shroud suction port 162a, into which air having passed through the first fan introducing portion 151 may be suctioned, may be formed and a second blade coupling portion that extends from the lower end portion in the upward direction.

A first surface of each blade 163 may be coupled to the first blade coupling portion of the hub 161 and a second surface thereof may be coupled to the second blade coupling portion of the shroud 162. The plurality of blades 163 may be disposed or provided spaced apart in a circumferential direction of the hub 161.

Each blade 163 may include a leading edge 163a, which forms a side end portion or side end, to which air is introduced, and a trailing edge 163b, which forms a side end portion or side end, from which air is output. The air having passed through the first filter 120 may be introduced to the first fan housing 150 through the first fan introducing portion 151 with the air flowing in the upward direction. The air may flow in the axial direction of the first fan 160, may be introduced to the first leading edge 163a, and may be output to the trailing edge 163b via the blade 163. The trailing edge 163b may extend at an inclined to the outside with respect to the axial direction in the upward direction corresponding to a flow direction of air so that the air which is output through the trailing edge 163b is capable of flowing to the upper side in the radial direction.

Reference to FIG. 5, the first blowing device 100 may further include a first air guide device or guide 170 which may guide a flow of air having passed through the first fan 160 by being coupled to the upper side of the first fan 160. The first air guide 170 may include an outer wall 171 having a cylindrical shape and an inner wall 172 positioned on or at an inside of the outer wall 171 and having a cylindrical shape. The outer wall 171 may be disposed or provided to surround the inner wall 172. A first air flow path 172a, through which air may flow, may be formed between an inner circumferential surface of the outer wall 171 and an outer circumferential surface of the inner wall 172.

The first air guide 170 may include a guide rib 175 which may be disposed or provided on or in the first air flow path 172a. The guide rib 175 may extend from the outer circumferential surface of the inner wall 172 to the inner circumferential surface of the outer wall 171. A plurality of guide ribs 175 may be disposed or provided spaced apart from each other. The plurality of guide ribs 175 may guide the air introduced to the first air flow path 172a of the first air guide 170 via the first fan 160 in the upward direction.

The guide rib 175 may extend at an incline from a lower portion of the outer wall 171 and the inner wall 172 in the upward direction. For example, the guide rib 175 may be rounded, and thus, guide air so that it flows at an incline in the upward direction.

That is, with reference to FIG. 6, the guide rib 175 may include a rib main body 175a, which may extend rounded in the upward direction. The rib main body 175a may include a positive pressurizing surface 175b which faces in a direction in which an air flow approaches and a negative pressuring surface 175c which is opposite to the positive pressurizing surface 175b. The positive pressurizing surface 175b may have a concave shape and the negative pressurizing surface 175c may have a convex shape.

The rib main body 175a may include a leading edge 175d which forms a side end portion or side end, to which air may be introduced, and a trailing edge 175e which forms a side end portion or side end, to which air may be discharged. The leading edge 175d may be rounded and bent from the positive pressurizing surface 175b toward the negative pressurizing surface 175c. According to this configuration, a portion of air which is introduced via the leading edge 175d may be guided to the positive pressurizing surface 175b and the rest of the air may be guided to the negative pressurizing surface 175c. Air which flows to the negative pressurizing surface 175c may pass by a plurality of projecting portions 175f.

The plurality of projecting portions 175f may project from the negative pressurizing surface 175c and may extend from the leading edge 175d toward the trailing edge 175e. The projecting portion 175f may have an airfoil shape a projecting height of which may be gradually reduced from the leading edge 175d toward the trailing edge 175e. Generation of a vortex on the negative pressurizing surface 175c may be prevented, and thus, air may easily flow toward the upper side, due to the plurality of projecting portions 175f formed on the negative pressurizing surface 175c.

The trailing edge 175e may have a saw tooth shape having peaks and valleys which may be repeated in the radial direction. According to this configuration, a difference between times at which air is output from the trailing edge 175e, that is, air is output from the peaks and valleys from each other may be generated, and thus, generation of noise may be reduced.

The first air guide 170 may further include a motor accommodating portion 173 that extends from the inner wall 172 to the lower side, and thus, accommodates the first fan motor 165. The motor accommodating portion 173 may have a bowl shape, a diameter of which may be gradually reduced in the downward direction. A motor coupling portion 166 may be provided on or at one side of the first fan motor 165 to fix the first fan motor 165 to the first air guide 170.

A shape of the motor accommodating portion 173 may correspond to the shape of the hub 161. The motor accommodating portion 173 may be inserted into the hub 161.

The first fan motor 165 may be supported to or at an upper side of the motor accommodating portion 173. The rotational shaft 165a of the first fan motor 165 may extend from the first fan motor 165 in the downward direction and be coupled to the shaft coupling portion 161a of the hub 161 through the lower surface portion of the motor accommodating portion 173.

Figure 8:
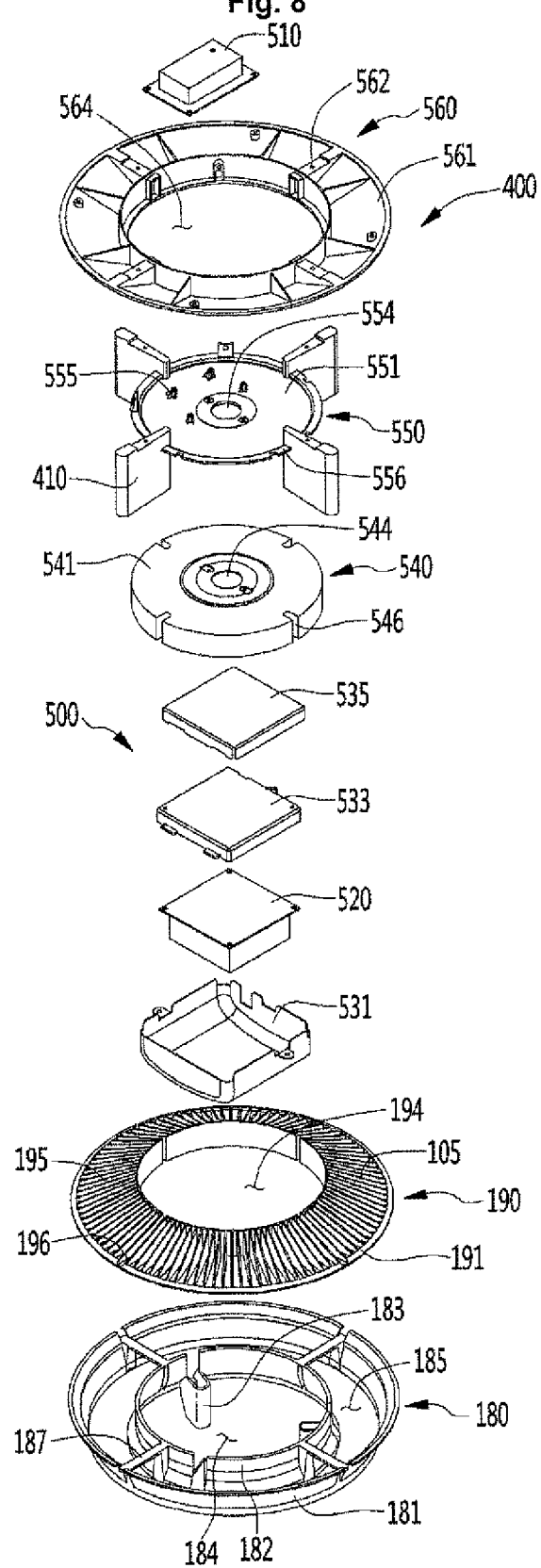
FIG. 8 is an exploded perspective view of a portion of the first blowing device and a dividing device of the air cleaner of FIG. 1.

FIG. 8 is an exploded perspective view a portion of the first blowing device and a dividing device of the air cleaner of FIG. 1. With reference to FIG. 2, FIG. 3, and FIG. 8, the first blowing device 100 of the air cleaner of FIG. 1 may further include a second air guide device or guide 180, which may be coupled to an upper side of the first air guide 170 and guide air having passed through the first air guide 170 to the first discharge guide 190.

The second air guide 180 may include a first guide wall 181, which may have a substantially cylindrical shape, and a second guide wall 182, which may be positioned at an inside of the first guide wall 181 and have a substantially cylindrical shape. The first guide wall 181 may be disposed or provided to surround the second guide wall 182.

A second air flow path 185, through which air may flow, may be formed between an inner circumferential surface of the first guide wall 181 and an outer circumferential surface of the second guide wall 182. Air which flows along the first air flow path 172a of the first air guide 170 may flow in the upward direction through the second air flow path 185.

A fastening guide 183, which may be coupled with the first air guide 170, may be provided on a lower portion of the second guide wall 182. The fastening guide 183 may extend to the lower side of the second guide wall 182.

A predetermined fastening member may be coupled to the fastening guide 183, and the fastening member may be coupled to a fastening rib 178 of the first air guide 170. The fastening rib 178 may project from an upper surface of the motor accommodating portion 173 in the upward direction. A plurality of fastening guides 183 and a plurality of fastening ribs 178 may be provided.

The second air guide 180 may further include a leg supporting portion or support 187 that extends from an inner circumferential surface of the first guide wall 181 to an outer circumferential surface of the second guide wall 182 and supports a leg 410, which is described hereinafter. The leg supporting portion 187 may include an upper surface which may support the lower surface of the leg 410. A plurality of leg supporting portions 187 may be provided.

A first space portion or space 184, in which at least a portion of a PCB device or PCB 500 may be accommodated, may be formed in or at an inside of the second guide wall 182 having a cylindrical shape. At least a portion of a PCB drive portion or drive 520 of the PCB device 500 may be positioned on or in the first space portion 184.

The first blowing device 100 may further include a first discharge guiding device or guide 190, which may be disposed or provided on or at an upper side of the second air guide 180, that is, an outlet side of air flow relative to the air flow and guide the air discharged to the outside of the air cleaner 10. The first discharge guide 190 may include a first discharge main body 191 which forms a second space portion or space 194 at a substantially central portion thereof. For example, the first discharge main body 191 may have an annular shape.

At least a portion of the PCB device 500 may be accommodated in the second space portion 194. For example, at least a portion of the PCB drive portion 520 of the PCB device 500 may be positioned in the second space portion 194. The second space portion 194 may be formed on or at an upper side of the first space portion 184 and form an installation space portion or space, in which the PCB device 500 may be provided along with the first space portion 184.

The first discharge main body 191 may include the first discharge grill 195. A plurality of the first discharge grill 195 may be provided and the first discharge portion or outlet 105, to which air may be discharged to the outside, may be formed between the plurality of first discharge grills 195. The plurality of the first discharge grills 195 may be disposed or provided on or at an upper side of the second air flow path 185 and the air having passed through the second air flow path 185 may flow to the first discharge grill 195 side and may be discharged through the first discharge portion 105.

The first discharge main body 191 may include a leg inserting portion or insert 196, which may be inserted into the leg 410. The leg inserting portion 195 may be formed between two of the plurality of the first discharging grills 195. A plurality of the leg inserting portions 196 may be provided corresponding to a number of the leg 410. The leg 410 may be inserted into the leg inserting portion 196, extend to a lower side, and thus, may be seated in the leg supporting portion 187.

The PCB device 500 may be provided on or at an upper side of the first discharge guide 190. The PCB device 500 may include a main PCB 510 and the PCB drive portion 520 that supplies power to drive the main PCB 510. The main PCB 510 and the PCB drive portion 520 may be electrically connected by wiring. The main PCB 510 may be positioned on or at an upper side of the PCB drive portion 520.

The PCB device 500 may further include a case assembly 531, 533, and 535 that protects the PCB drive portion 520. The case assembly 531, 533, and 535 may include a first case 531, in which the PCB drive portion 520 may be seated, a second case 535 that covers an upper side of the PCB drive portion 520, and an insulating member or insulator 533, which may be provided between the PCB drive portion 520 and the second case 535.

The first case 531 and the second case 535 may protect the PCB drive portion 520 and may be made of an incombustible material in order to prevent a fire from being generated in other components provided inside of the air cleaner 10 by heat generated in the PCB drive portion 520. For example, the first case 531 or the second case 535 may be made of a steel material.

The insulating member 533 may be provided at an upper surface of the PCB drive portion 520. The insulating member 533 may protect the PCB drive portion 520 and prevent electric current leaking from the PCB drive portion 520 from being transferred to another component, that is, perform an insulating function. For example, the insulating member 533 may be made of ABS resin (acrylonitrile-butadiene-styrene copolymer).

The PCB device 500 may further include a PCB cover 540 which may be provided in or at an upper side of the second case 535. The PCB cover 540 may cover an upper side of the second space portion 194, and thus, communication between the first space portion 184 and second space portion 194 and the first discharge portion 105 may be blocked. Accordingly, air which is discharged from the first discharge portion 105 may be prevented from being introduced to the first and the second space portions 184 and 194 by the PCB cover 540.

The PCB cover 540 may include a cover main body 541 having a cap shape. The cover main body 541 may easily shield the upper side of the first space portion 184 and the second space portion 194 by the cap shape.

A first through hole 544, through which wiring or a harness provided on or at an inside portion or inside of the air cleaner 10 may pass, may be formed on the cover main body 541. The first through hole 544 may be formed on or at a substantially central portion of an upper surface portion or surface of the cover main body 541.

The harness may be wiring bundles. The wiring or the harness may include wiring that connects the main PCB 510 and the PCB drive portion 520 or wiring that connects components requiring an electric connection, such as the fan motor and a display device or display.

A first leg groove 546 may be formed on or at an outer circumferential surface of the cover main body 541. The first leg groove 546 may have a shape which is depressed from the outer circumferential surface of the cover main body 541 and may be configured so that at least a portion of the leg 410 may be inserted into the first leg groove 546. A plurality of the first leg grooves 546 may be provided corresponding to a number of the leg 410.

The PCB device 500 may further include a PCB supporting portion or support 550, which may be provided on or at an upper side of the PCB cover 540 and to which the main PCB 510 may be coupled. The PCB supporting portion 550 may have a substantially dish shape and may be gradually narrowed toward a lower portion thereof. The main PCB 510 may be supported by an upper surface 551 of the PCB supporting portion 550.

A fixing projection 555 that fixes the PCB supporting portion 550 may be included in or on an upper surface of the PCB supporting portion 550. A predetermined fastening member may be coupled to the fixing projection 555. The fastening member may couple the main PCB 510 and the fixing projection 555 with each other.

A second through hole 554 that communicates with the first through hole 544 and through which the wiring or the harness may pass may be formed at a substantially central portion of the PCB supporting portion 550. When the PCB supporting portion 550 and the PCB cover 540 are coupled, the second through hole 554 and the first through hole 544 may be aligned with each other in the vertical direction. The wiring or the harness may pass through the aligned first through hole 544 and second through hole 554.

A second leg groove 556, into which at least a portion of the leg 410 may be inserted, may be formed on or at a rim portion or rim of the PCB supporting portion 550. The leg 410 may be coupled to the PCB cover 540 and the PCB supporting portion 550 through the first leg groove 546 and the second leg groove 556, pass through the leg inserting portion 196 of the first discharge guide 190, and thus, may be supported by the leg supporting portion 187 of the second air guide 180.

The PCB device 500 may further include a lever supporting device or support 560, which may be coupled to an upper side of the leg 410 and support the lever device 242 of the second blowing device 200. The lever supporting device 560 may have a substantially annular shape. The lever supporting device 560 may include a third space portion or space 564, which may define an installation space in which the PCB supporting portion 550 and the main PCB 510 may be positioned. The third space portion 564 may be formed at a substantially central portion of the lever supporting device 560.

The lever supporting device 560 may further include a leg coupling portion 562, which may be coupled to an upper portion of the leg 410. The lever coupling portion 562 may be provided on or at a rim portion or rim of the lever supporting device 560 and a plurality of leg coupling portions 562 may be provided corresponding to a number of the leg 410. In other words, an upper end portion or end of the leg 410 may be coupled to the leg coupling portion 562 and a lower end portion or end thereof may be supported by the leg supporting portion 187 of the second air guide 180.

The lever supporting device 560 may further include a blocking portion 561 by which introduction of air discharged through the first discharge portion 105 to the second blowing device 200 may be blocked. The blocking portion 561 may be understood as a main body portion of the lever supporting device 560 having an annular shape.

The dividing device 400 may be provided between the first blowing device 100 and the second blowing device 200. The dividing device 400 may include the leg 410 that spaces apart the first blowing device 100 and the second blowing device 200 from each other.

A separation space may be defined between the first blowing device 100 and the second blowing device 200 by the leg 410. A plurality of legs 410 which are spaced apart from each other in the circumferential direction may be provided. The leg 410 may extend from a lower portion toward an upper portion of the separation space, that is, in the axial direction.

The air which is discharged from the first blowing device 100, that is, the air which is discharged from the first discharging portion 105 of the first discharge guide 190 may easily flow through the separation space.

The dividing device 400 may further include a blocking wall 430, which may be installed or provided between the plurality of legs 410 and extend in the radial direction, that is, in the transverse direction. The separation space may be divided into an upper space and a lower space by the blocking wall 430.

The air which is discharged from the first discharge portion 105 may be discharged outside of the air cleaner 10 via a lower space of lower side of the blocking wall 430. The air which is discharged from the first discharge portion 105 may be prevented from being introduced to the second blowing device 200 side by the blocking wall 430.

The PCB device 500 may be disposed or provided in the separation space, which may be divided by the dividing device 400, and thus, may be understood as a configuration of the dividing device 400.

Figure 9:
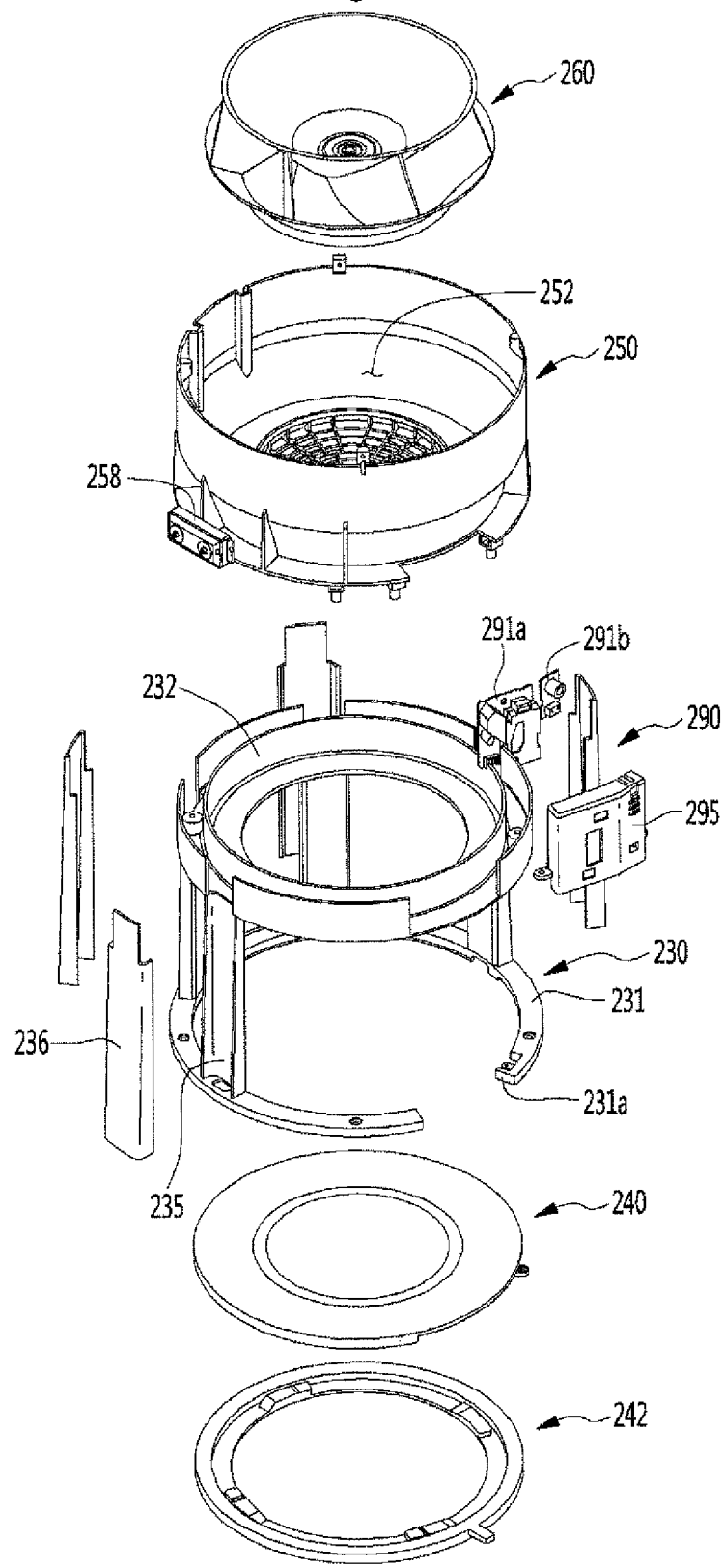
FIG. 9 and FIG. 10 are exploded perspective views of a second blowing device of the air cleaner of FIG. 1.
Figure 10:
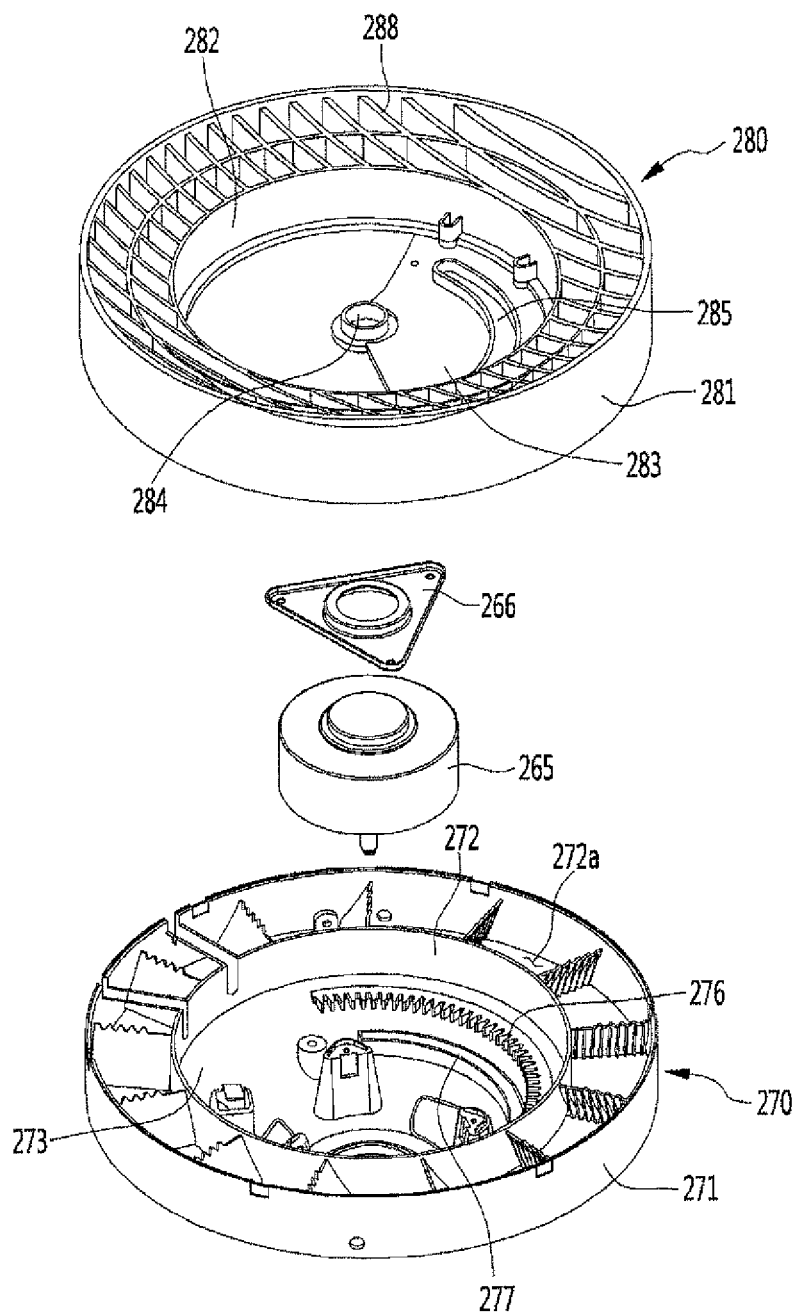
Figure 11:
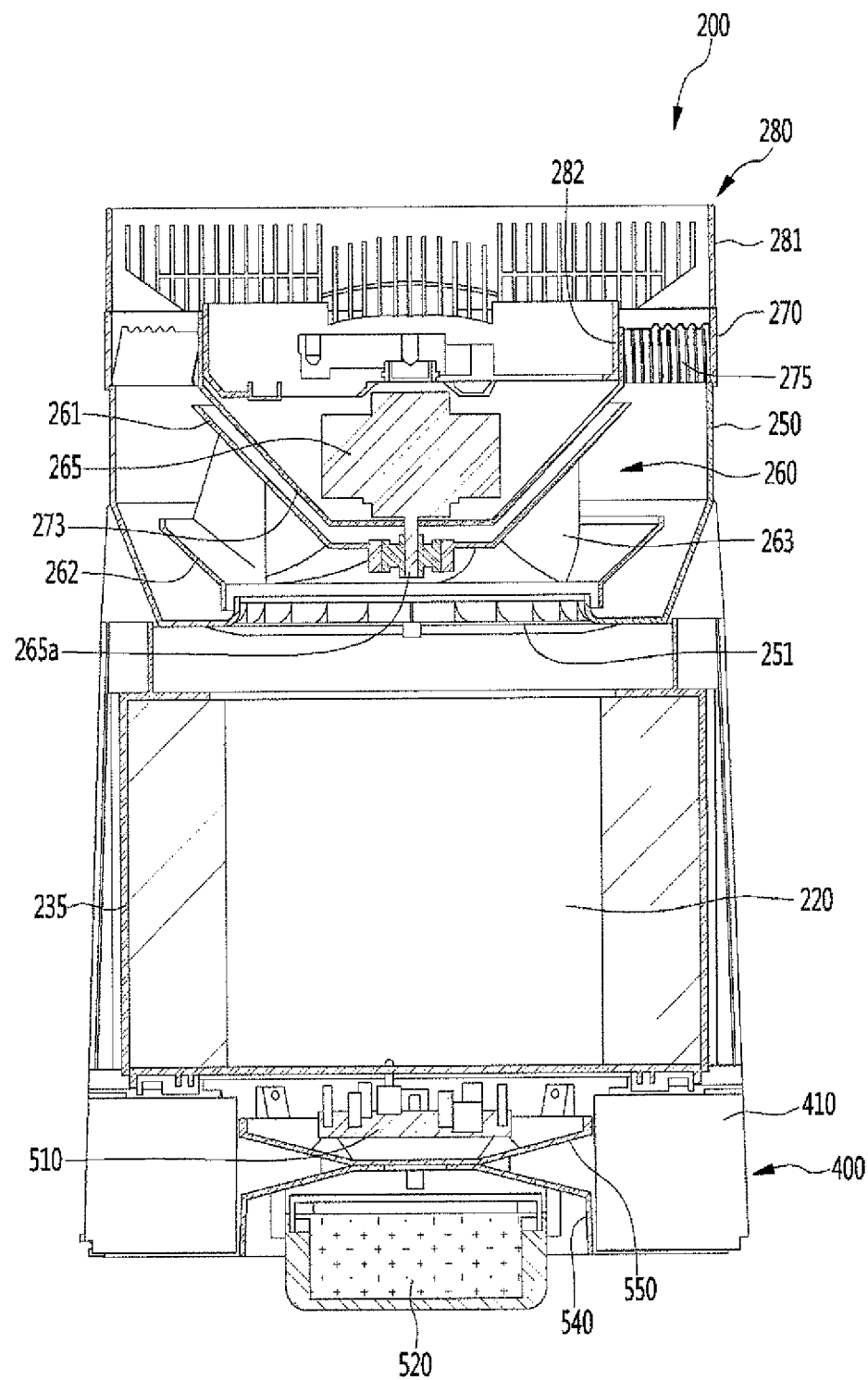
FIG. 11 is a cross-sectional view of the second blowing device of the air cleaner of FIG. 1.

FIG. 9 and FIG. 10 are an exploded perspective views of a second blowing device of the air cleaner of FIG. 1. FIG. 11 is a cross-sectional view of the second blowing device of the cleaner of FIG. 1.

With reference to FIG. 2, FIG. 3, and FIG. 9 to FIG. 11, the second blowing device 200 may include a supporting device or support 240, a lever device or lever 242, a second filter 220, a second filter frame 230, a second fan housing 250, and a second fan 250. This configuration is similar to that provided in the first blowing device 100 and repetitive disclosure has been omitted. Hereinafter, this configuration will be described.

The supporting device 240 may be provided to be movable between an upper side and a lower side by operation of a handle which may be provided on the lever device 242, and thus, support the second filter 220. When the supporting device 240 moves to the upper side, the second filter 220 may be in a state of being coupled to the second blowing device 200. In contrast, when the supporting device 240 moves to the lower side, the second filter 220 may be in a state (released state) of being separable from the second blowing device 200, that is, in a released state.

The lever device 242 may include a lever projecting portion and the supporting device 240 may include a support projecting portion, as illustrated in the lever device 142 and the supporting device 140 of the first blowing device 100. The supporting device 240 may be moved in the upward direction or in the downward direction by the lever projecting portion and the support projecting portion interacting with each other. A detailed description is provided with respect to the first blowing device 100.

The second filter 220 may have a cylindrical shape. The air, which is suctioned in through the second suction portion 202 of the second case 201, may flow inside of the second filter 220 by passing through an outer circumferential surface of the second filter 220. In other words, the second filter 220 may have a cylindrical shape and may have a filter surface that filters air.

The second filter frame 230 may include a first frame 231 that forms a lower portion of the second filter frame 230 and forms a handle space portion or space 231a, a second frame 232 that forms an upper portion of the second filter frame 230, a second filter supporting portion or support 235 that extends toward the second frame 232 in the upward direction, and a second supporting cover 236 that covers the second filter supporting portion 235. The second filter member 220 and the second filter frame 230 may be the same as or similar to the first filter member 120 and the first filter frame 130 of the first blowing device 100, and thus, repetitive disclosure has been omitted.

The second blowing device 200 may further include a sensor device or sensor 290. The sensor 290 may include a dust sensor 291a that detects an amount of dust in the air and a gas sensor 291b that detects an amount of gas in the air. The sensor 290 may further include a sensor cover 295 that covers at least one side of the sensors 291a and 291b. For example, the sensors 291a and 291b may be supported by the second frame 232 of the second filter frame 230.

The second fan housing 250 may include a second fan accommodating portion 252, in which the second fan 260 may be accommodated. The second fan housing 250 may include a second fan introducing portion 251, which may be provided on or at a lower portion of the second fan housing 250 and which may guide introduction of air to an inside portion or inside of the second fan housing 250.

The second fan 260 may include a hub 261, to which a rotational shaft 265*a* of the second fan motor 265 which may be a centrifugal fan motor may be coupled, a shroud 262, which may be spaced apart from the hub 261, and a plurality of blades 263, which may be provided between the hub 261 and the shroud 262. The second fan housing 250 and the second fan 260 may be the same or similar to the first fan housing 150 and the first fan 160 of the first blowing device 100, and thus, repetitive disclosure has been omitted.

The second blowing device 200 may further include an ionizer 258 that removes or sterilizes smell particles or odor in the air. The ionizer 258 may be coupled to the second fan housing 250 and be capable of acting on the air which flows inside of the second fan housing 250.

In this embodiment, although it is described that the sensor device 290 and the ionizer 258 are provided only in the second blowing device 200, the sensor device and the ionizer may also be installed or provided in or on the first blowing device. For example, the sensor device may be provided to or on the first filter frame 130 of the first blowing device and the ionizer may be installed or provided in or on the first fan housing of the first blowing device.

The second blowing device 200 may include a third air guide device or guide 270 that guides a flow of air having passed through the second fan 260 by being coupled to an upper side of the second fan 260. The third air guide 270 may include an outer wall 271 having a cylindrical shape and an inner wall 272 positioned inside of the outer wall 271 and having a cylindrical shape. A first air flow path 272*a*, through which air may flow, may be formed between an inner circumferential surface of the outer wall 271 and an outer circumferential surface of the inner wall 272.

The third air guide 270 may include a guide rib 275 which may be disposed or provided on or in the first air flow path 272*a*. The guide rib 275 may extend from the outer circumferential surface of the inner wall 272 to the inner circumferential surface of the outer wall 271.

The third air guide 270 may further include a motor accommodating portion 273 that extends from the inner wall 272 in a downward direction, and thus, may accommodate the second fan motor 265. The motor accommodating portion 273 may have a bowl shape a diameter of which may be gradually reduced toward a lower side.

The second fan motor 265 may be coupled to an upper side of the second fan 260, and thus, may provide a drive force to the second fan 260. A motor coupling portion 266 may be provided on or at one side of the second fan motor 265 and the motor coupling portion 266 may be fix the second fan motor 265 to the third air guide 270.

The outer wall 271, the inner wall 272, the guide rib 275, and the motor accommodating portion 273 of the third air guide 270 may be the same as or similar to the first air guide 170, and thus, repetitive disclosure has been omitted. The second fan motor 265 and the motor coupling portion 266 may be the same as or similar to the first fan motor 165 and the motor coupling portion 166, and thus, repetitive disclosure has been omitted.

The third air guide 270 may include guides 276 and 277 that guide a movement of the flow adjusting device 300. The guides 276 and 277 may include a first rack 276 and a shaft guide groove 277, which may be included in the motor accommodating portion 273.

The first rack 276 may be linked to the first gear 360 of the flow adjusting device 300. The first rack 276 may be provided on or at an inner circumferential surface of the motor accommodating portion 273 and may be provided along a set curvature in the circumferential direction. A length of the first rack 276 may be a length which is set based on a distance linked to the first gear 360.

The flow adjusting device 300 may be rotated in a lateral direction, that is, in the clockwise direction or counterclockwise direction. The first gear 360 may be rotated along a predetermined rotating radius about the rotational shaft 354 of the flow adjusting device 300.

The shaft guide groove 277 may be a groove that guides rotation of the first gear 260 and may extend to be rounded with a predetermined curvature. For example, the shaft guide groove 277 may be rounded in the circumferential direction. In other words, the shaft guide groove 277 may have an arc shape.

The first gear shaft 362 of the first gear 360 may be inserted into the shaft guide groove 277. In a process of rotation of the first gear 360, the first gear shaft 362 may be moved along the shaft guide groove 277.

The second blowing device 200 may include a second discharge guide device or guide 280, which may be installed or provided on or at an upper side of the third air guide 270 and guide a flow of air having passed through the third air guide 270. The second discharge guide 280 may have a substantially annular shape, an inside portion of which may be empty. That is, the second discharge guide 280 may include a discharge outside wall 281, which may form an outer circumferential surface of the second discharge guide 280 and a cylindrical shape and a discharge inner wall 282 that forms an inner circumferential surface of the second discharge guide 280 and has a cylindrical shape.

The discharge outer wall 281 may surround the discharge inner wall 282. A discharge flow path along which a flow of air passing through the third air guide 270 flows may be formed between an inner circumferential surface of the discharge outer wall 281 and an outer circumferential surface of the discharge inner wall 282. The discharge flow path may be positioned on or at an upper side of the air flow path in which the guide rib 275 is provided.

The second discharge guide 280 may further include a second discharge grill 288 which may be disposed or provided on or in the discharge flow path. The second discharge grill 288 may extend from the outer circumferential surface of the discharge inner wall 282 to the inner circumferential surface of the discharge outer wall 281.

The second discharge guide 280 may further include a rotational guide plate 283, which may be coupled to the discharge inner wall 282. The rotational guide plate 283 may extend from the inner circumferential surface of the discharge inner wall 282 toward an inside center of the second discharge guide 280.

The rotational guide plate 283 may include a shaft inserting portion 284, which may provide a rotation center in the lateral direction of the flow adjusting device 300. The rotational shaft 354 may be inserted into the shaft inserting portion 284. The shaft inserting portion 284 may be positioned in an inside central portion of the second discharge guide 280. The rotating guide plate 283 may be a supporting plate that supports the shaft inserting portion 284.

The rotational guide plate 283 may further include a bearing groove 285. A first bearing 353, which may be provided on the flow adjusting device 300, may be inserted into the bearing groove 285. The bearing groove 285 may be a groove that guides movement of the first bearing 353 and may extend to be rounded with a predetermined curvature. For example, the bearing groove 285 may be formed to be rounded in the circumferential direction. In other words, the bearing groove 285 may have an arc shape. In a process of rotating of the flow adjusting device 300 in the lateral direction, the first bearing 353 may be moved by being inserted into the bearing groove 285, and thus, allows a friction force, which is generated in the process of rotation of the flow adjusting device 300, to be reduced.

Figure 12:
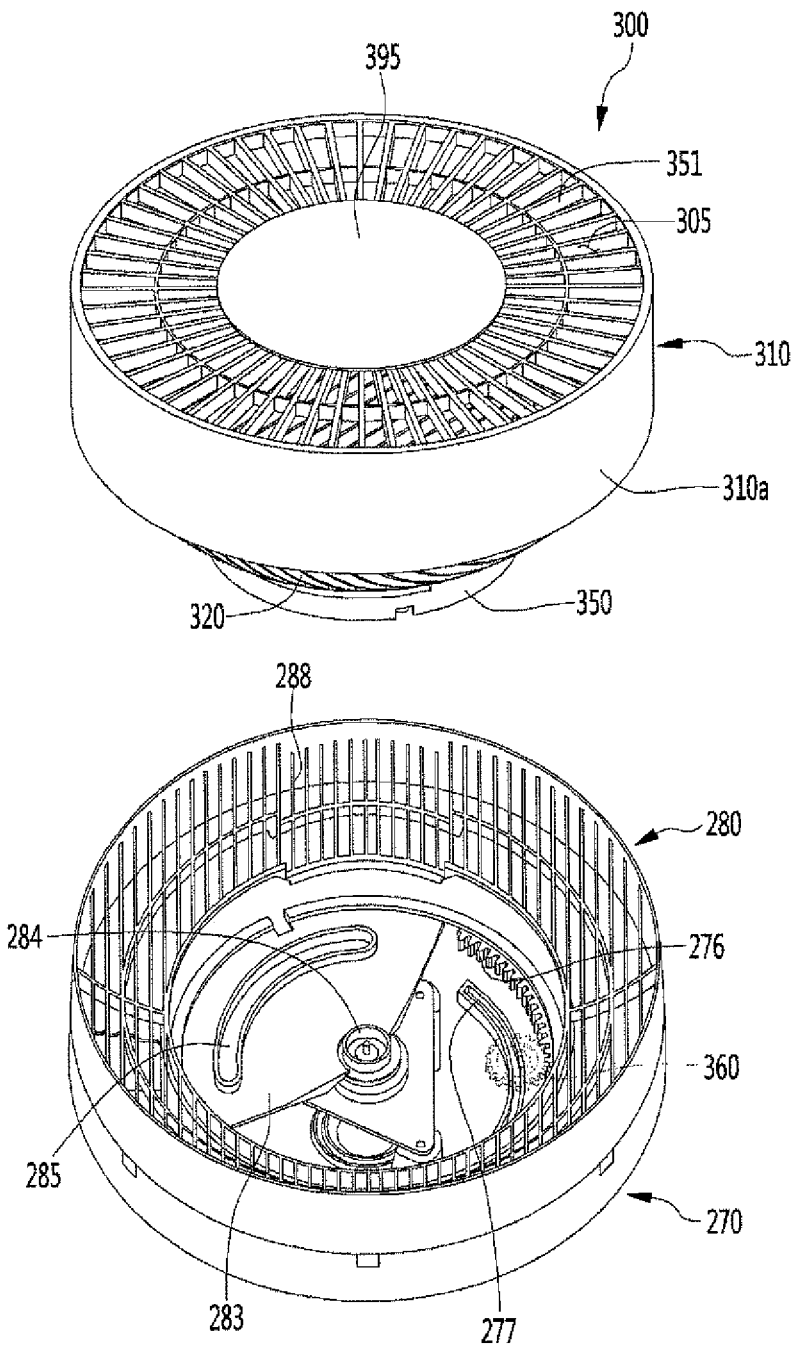
FIG. 12 is an exploded perspective view of a flow adjusting device and a component to which the flow adjusting device is coupled of the air cleaner of FIG. 1.
Figure 13:
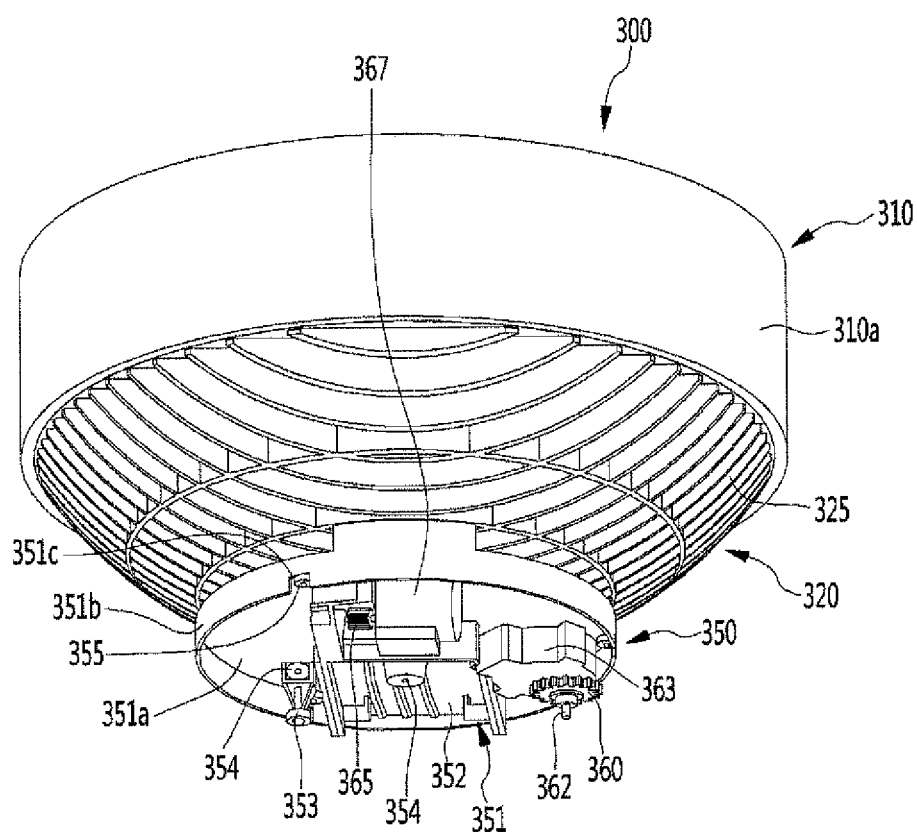
FIG. 13 is a perspective view of the flow adjusting device of FIG. 12.
Figure 14:
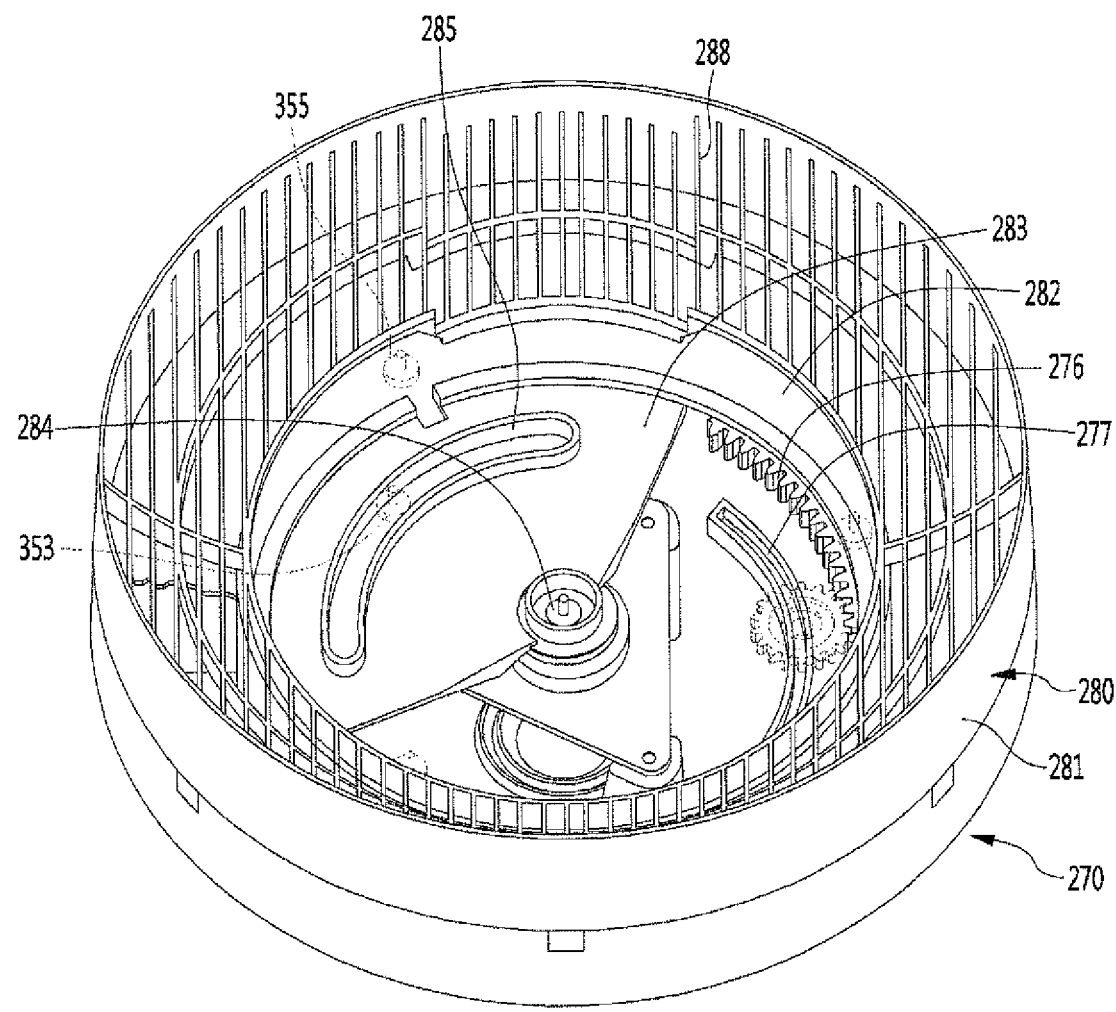
FIG. 14 is a view illustrating a coupling state between a third air guide and a second discharge guide of the air cleaner of FIG. 1.
Figure 15:
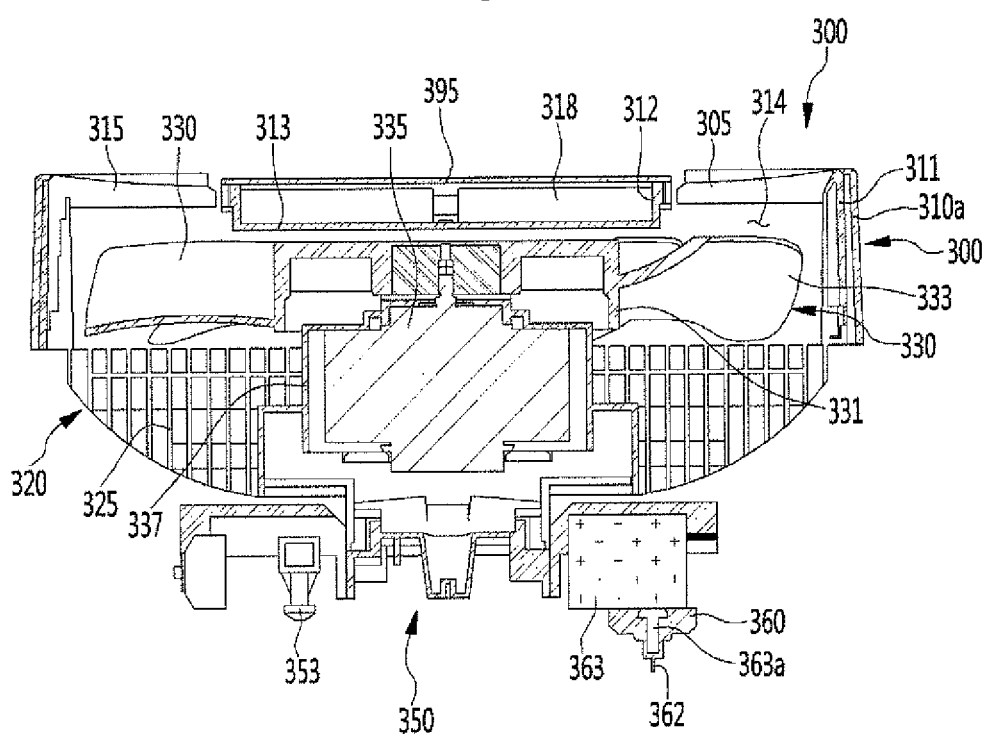
FIG. 15 is a cross-sectional view of the flow adjusting device of FIG. 12.

FIG. 12 is an exploded perspective view of a flow adjusting device and a component to which the flow adjusting device is coupled of the air cleaner of FIG. 1. FIG. 13 is a perspective view of the flow adjusting device of FIG. 12. FIG. 14 is a view illustrating a coupling state between a third air guide and a second discharge guide of the air cleaner of FIG. 1. FIG. 15 is a cross-sectional view of the flow adjusting device of FIG. 12.

FIG. 12 to FIG. 15 are views illustrating a configuration for guiding rotation of the flow adjusting device 300 in the lateral direction. The flow adjusting device 300 may include a third fan housing 310 in which the third fan 330 may be accommodated. The third fan housing 310 may have a substantially annular shape.

The third fan housing 310 may include a housing case 310*a* that forms an outer appearance thereof. The housing case 310*a* may be a fixed configuration. Housing main bodies 311 and 312 may be rotatably provided inside of the housing case 310*a*. In other words, the housing case 310*a* may surround the housing main bodies 311 and 312.

That is, the housing main bodies 311 and 312 may include a housing outer wall 311 which may have an outer circumferential surface and a cylindrical shape and a housing inner wall 312 which may be positioned inside of the housing outer wall 311 and have a cylindrical shape. The housing outer wall 311 may surround the housing inner wall 312. A housing flow path 314 in which an air flow may be formed between an inner circumferential surface of the housing outer wall 311 and an outer circumferential surface of the housing inner wall 312.

A shielding portion or shield 313 that covers an upper side of the third fan 330 and shields the flow of air may be provided on or at a lower portion of the housing inner wall 312. The housing inner wall 312 and the shielding portion 313 may be coupled to each other and have a substantially U shape.

An installation space, in which the third fan 330 may be installed or provided, may be formed on or at an inside portion of the third fan housing 310. The third fan housing 310 may include a discharge grill 315 that forms a second discharge portion or outlet 305 through which air passing through the third fan 330 may be discharged. The discharge grill 315 may have a substantially annular shape and may be coupled to an upper side of the housing flow path 314. The air passing through the housing flow path 314 may be discharged to the outside of the air cleaner 10 via the second discharge portion 305 of the discharge grill 315. In the air cleaner 10, a discharge blowing amount may be improved and air may be discharged in various directions as the second discharge portion 305 along with the first discharge portion 105 of the first blowing device 100 may be provided.

A top cover 395 may be installed or provided on or at an upper side of the housing inner wall 312. A display device or display, on which operating information of the air cleaner 10 may be displayed, may be provided on the top cover 395. A display PCB 318 may be installed or provided on or at a lower side space of the top cover 395. In other words, the housing inner wall 312, the shielding portion 313, and the top cover 395 may form a closed space and the display PCB 318 may be installed or provided in the closed space.

An axial flow fan may be included as the third fan 330 which may be installed or provided inside of the third fan housing 310. That is, the third fan 330 may be operated in order to axially discharge air which is axially introduced. In other words, the air which flows toward the third fan 330 in the upward direction via the second fan 260, the first air flow path 272*a* of the third air guide 270, and the discharge flow path of the second discharge guide 280 may be discharged from the third fan 330, and thus, may be discharged to the outside through the second discharge portion 305, which may be positioned on or at the upper side of the third fan 330.

The third fan 330 may include a hub 331 having a shaft coupling portion to which a rotational shaft 336 of the third fan motor 335 may be coupled and a plurality of blades 333 coupled to the hub 331 in the circumferential direction. The third fan motor 335 may be coupled to a lower side of the third fan 330 and may be disposed or provided on or at an inside of the third motor housing 337.

The first fan motor 165 and the second fan motor 265 may be disposed or provided in series relative to a longitudinal direction of the air cleaner 10. The second fan motor 265 and the third fan motor 335 may be disposed or provided in series relative to the longitudinal direction of the air cleaner 10. In summary, the rotational shafts of the first fan motor 165, the second fan motor 265, and the third fan motor 335, or the first fan 160, the second fan 260, and the third fan 330 may be positioned on a same axis in the longitudinal direction.

The flow adjusting device 300 may further include a flow guide portion or guide 320, which may be coupled to a lower side of the third fan housing 310, and thus, guide the air passing by the second discharge guide 280 to the third fan housing 310. The flow guide 320 may include an introduction grill 325 which may guide the air introduction to the third fan housing 310. The introduction grill 325 may have a concave shape in the downward direction.

A shape of the second discharge grill 288 of the second discharge guide 280 may be formed in a concave shape in the downward direction corresponding to the shape of the introduction grill 325. The introduction grill 325 may be seated on or at an upper side of the second discharge grill 288. By this configuration, the introduction grill 325 may be stably supported by the second discharge grill 288.

The flow adjusting device 300 may further include a rotation guide device or guide 350 which may be installed or provided on or at a lower side of the flow guide 320, and thus, guide rotation in the lateral direction and rotation in the vertical direction of the flow adjusting device 300. The rotation in the lateral direction may be referred to as a "first direction rotation" and the rotation in the vertical direction may be referred to as a "second direction rotation".

The rotation guide 350 may include a guide main body 351 which may be coupled to the flow guide 320, a first guide that guides the first direction rotation of the flow adjusting device 300, and a second guide that guides the second direction rotation of the flow adjusting device 300. The guide main body 351 may include a lower surface portion or surface 351*a*, on which the first and the second guides may be installed or provided, and a rim portion or rim 351*b*, which may be provided to or at a rim of the lower surface portion 351*a* and may project toward the lower side.

The first guide may include a first gear motor 363 that generates a driving force and a first gear 360 which may be rotatably coupled to the first gear motor 363. For example, the first gear motor 363 may include a step motor, a rotational angle of which may be easily controlled.

The first gear 360 may be coupled to a motor shaft 363a of the first gear motor 363. The first guide may include a first gear shaft 362 that extends from the first gear 360 in the downward direction, that is, toward the third air guide 270 or the second discharge guide 280.

The first gear 360 may be geared to the first rack 276 of the third air guide 270. A plurality of gear teeth may be formed in the first gear 360 and the first rack 276. When the first gear motor 363 is driven, the first gear 360 may rotate, and thus, links to the first rack 276. The third air guide 270 may be a fixed configuration, and thus, the first gear 360 may be movable.

The shaft guide groove 277 of the third air guide 270 may guide movement of the first gear 360. That is, the first gear shaft 362 may be inserted into the shaft guide groove 277. The first gear shaft 362 may be moved along the shaft guide groove 277 in a rotation process of the first gear 360.

The first guide mechanism may further include a rotational shaft 354, which may be a rotational center of the flow adjusting device 300. The first gear 360 and the first gear shaft 362 may be rotated along a rotating radius which may be set about the rotating shaft 354. The set rotating radius may be referred to as a "first rotating radius".

The first rack 276 and the shaft guide groove 277 may have a length corresponding to a rotational amount or rotational angle of the flow adjusting device 300. The rotational shaft 354 may be included in the lower surface portion 351a of the guide main body 351. That is, the rotational shaft 354 may project from the lower surface portion 351a in the downward direction. The rotational shaft 354 may be inserted into the shaft inserting portion 284 of the second discharge guide 280 and may be rotated in the shaft inserting portion 284.

In other words, when the first gear 360 rotates, the first gear shaft 362 and the first gear 360 rotate about the rotational shaft 354 in the circumferential direction. The rotating shaft 354 may rotate in the shaft inserting portion 284. Accordingly, the flow adjusting device 300 may be rotated in a first direction, that is, in the clockwise direction or in the counterclockwise direction about the longitudinal or axial direction.

The first guide may further include bearings 353 and 355 that easily rotate the flow adjusting device 300 in the first direction. The bearings 353, 355 may reduce a friction force which is generated in the rotation process of the flow adjusting device 300.

The bearings 353 and 355 may include the first bearing 353 provided in the lower surface portion 351a of the guide main body 351. For example, the first gear motor 363 may include a ball bearing. The first guide mechanism may further include a bearing supporting portion or support 354 that projects from the lower surface portion 351a in the downward direction, and thus, supports the bearing 353.

The bearing supporting portion 354 may have a set or predetermined length, and thus, allow the first bearing 353 to be disposed in a position in which it is in contact with the rotation guide plate 283. The rotation guiding plate 283 may include the bearing groove 285 into which the first bearing 353 may be inserted. In a process of rotation of the flow adjusting device 300 in the first direction, the first bearing 353 may be movable while inserted into the bearing groove 285.

The first bearing 353 may be rotated along a rotating radius which is set about the rotating shaft 354. The set rotating radius may be referred to as a "second rotating radius". The second rotating radius may be less than the first rotating radius. In other words, a distance from the rotational shaft 354 to the first bearing 353 may be less than a distance from the rotational shaft 354 to the first gear shaft 362.

In summary, when the first gear shaft 362 moves along the shaft guide groove 277, the first bearing 353 may be moved along the bearing groove 285. For smooth movement of the first bearing 353 and the first gear shaft 362, a set or predetermined curvature of the shaft guide groove 277 and a set or predetermined curvature of the bearing groove 285 may be the same.

The bearings 353 and 355 may further include a second bearing 355. The second bearing 355 may be rotatably installed or provided on the rim portion 351b. The rim portion 351b may form a bearing inserting portion 351c, to which the second bearing 355 may be coupled. A plurality of second bearings 355 may be provided.

The second bearing 355 may be in contact with the discharge inner wall 282 of the second discharge guide 280, that is, the inner circumferential surface of the discharge inner wall 282 may form a contact surface of the second bearing 355. The flow adjusting device 300 may be easily rotated in the first direction by the second bearing 355 rotating about the rotational shaft 354 along the inner circumferential surface of the discharge inner wall 282.

Figure 16:
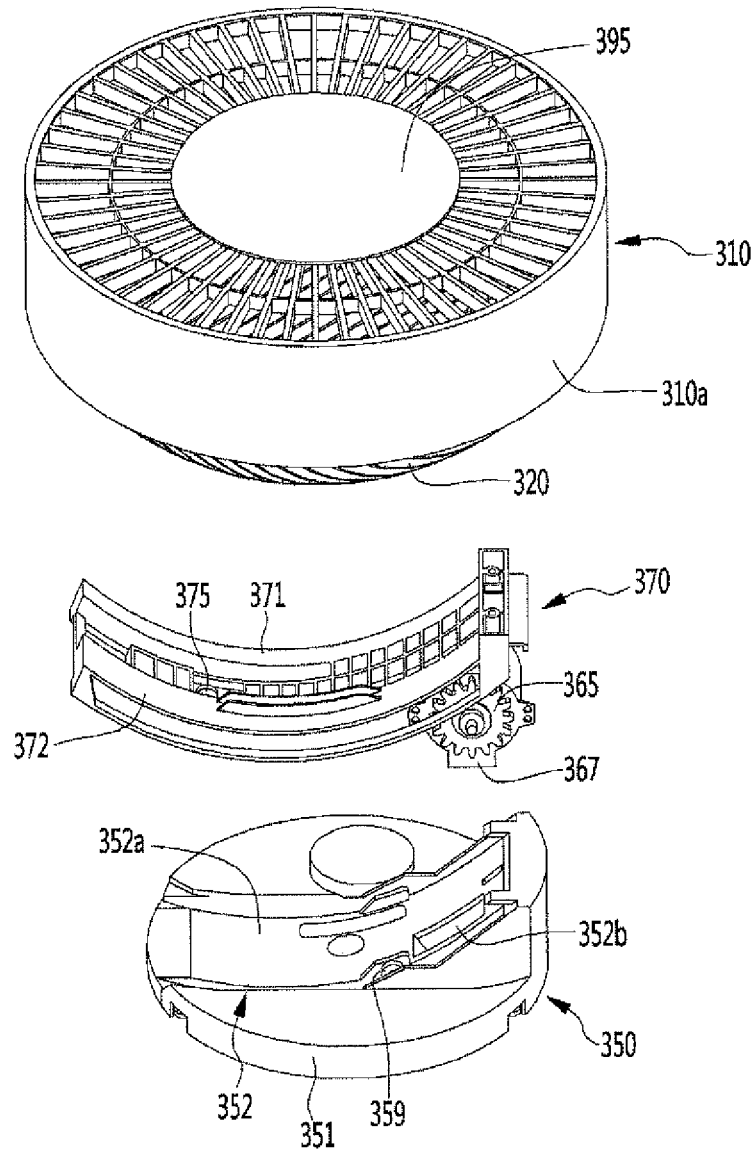
FIG. 16 is an exploded perspective view of the flow adjusting device of FIG. 12.
Figure 17:
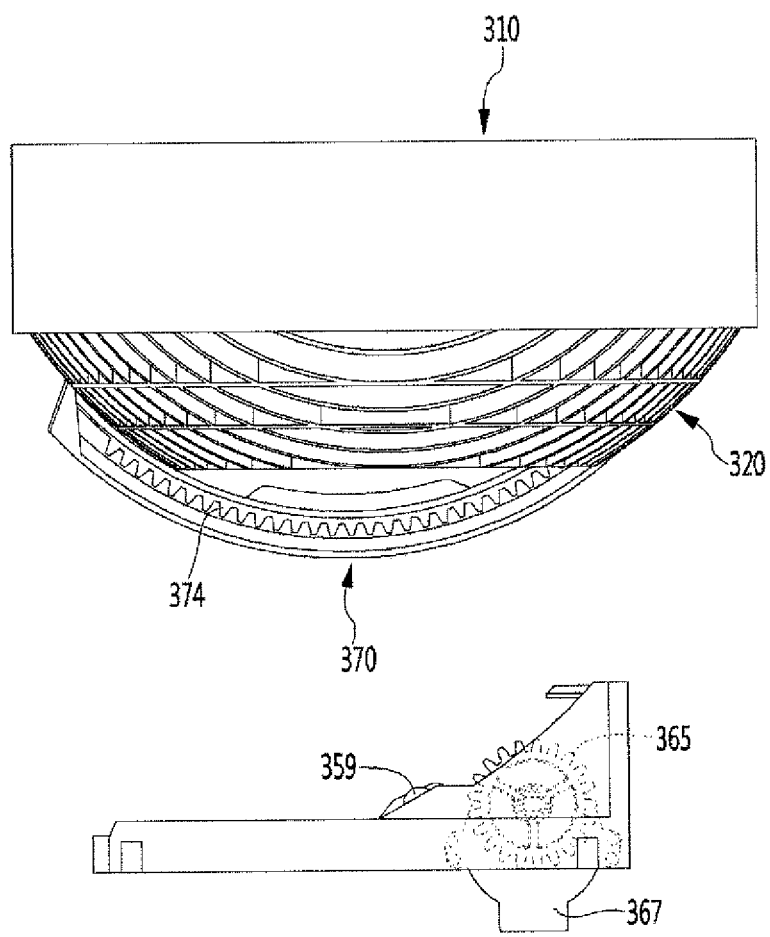
FIG. 17 is an exploded perspective view of a driving portion and a fixing portion of the flow adjusting device of FIG. 12.
Figure 18:
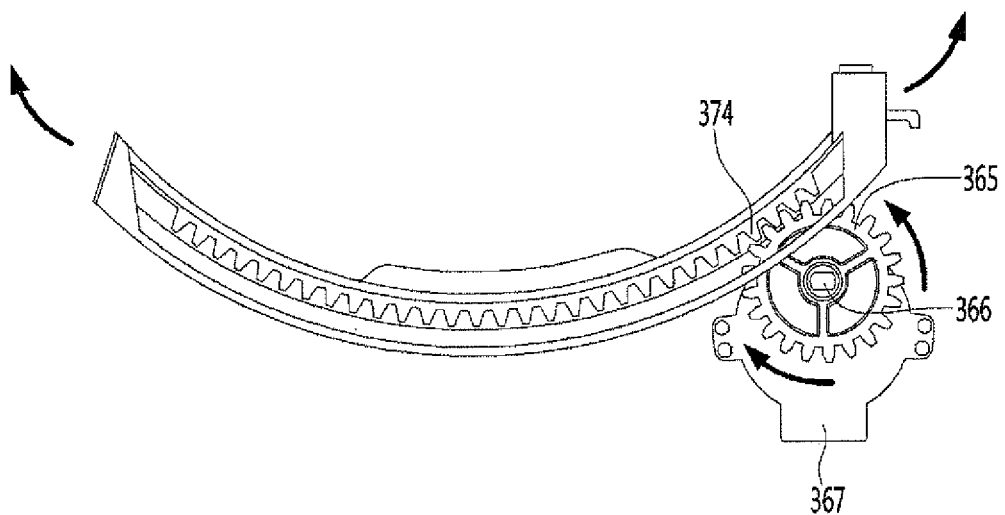
FIG. 18 is a view illustrating a linked state between a second rack and a second gear provided in the flow adjusting device of FIG. 12.

FIG. 16 is an exploded perspective view of the flow adjusting device of FIG. 12. FIG. 17 is an exploded perspective view of a driving portion and a fixing portion of the flow adjusting device of FIG. 12. FIG. 18 is a view illustrating a linked state between a second rack and a second gear provided in the flow adjusting device of FIG. 12. FIG. 19 to FIG. 21 are views illustrating a state in which the flow adjusting device of FIG. 12 is in a second position.

With reference to FIG. 16 to FIG. 18, the second guide according to this embodiment may include a fixing guide 352, which may be fixed to the guide main body 351. The center shaft 354 may be provided in a lower surface of the fixing guide 352.

The fixing guide 352 may include a first guide surface 352a, which may guide rotation in the second direction of the rotating guide 350. The first guide surface 352a may be rounded to an upper side corresponding to a rotating path of the rotating guide 350.

The fixing guide 352 may further include a first guide bearing 359, which may reduce a friction force generated at a time of a rotating movement of the rotation guide 350 by being provided in contact with the rotation guide 350. The first guide bearing 359 may be positioned to or at a side of the first guide surface 352a.

The fixed guide 352 may further include a second gear inserting portion 352b into which the second gear 365 may be inserted for rotation of the rotation guide 350. The second gear inserting portion 352b may be formed on or at one side of the first guide surface 352a. For example, the second gear inserting portion 352b may have a shape of a cut out of at least a portion of the first guide surface 352a. The second gear 365 may be positioned to or at a lower side of the first guide surface 352a and at least a portion of the second gear 365 may be configured to project to an upper side of the second gear inserting portion 352b through the second gear inserting portion 352b.

The second guide mechanism may further include a second gear motor 367, which may be coupled to the second gear 365 and provide a driving force. For example, the second gear motor 367 may include a step motor. The second guide may further include a second gear shaft 366 that extends from the second gear motor 367 to the second gear 365. When the second gear motor 367 is driven, the second gear shaft 366 and the second gear 365 may be rotated together.

The second guide may further include a rotation guide 370, which may be provided on or at an upper side of the fixing guide 352. The rotating guide 370 may be coupled to a lower side of the flow guide 320.

That is, the rotation guide 370 may include a main body 371, which may be supported by the fixing guide 352. The main body 371 may include a second guide surface 372, which may move along the first guide surface 352a. The second guide surface 372 may be rounded corresponding to a curvature of the first guide surface 352a.

The rotation guide 370 may further include a second guide bearing 375, which may reduce a friction force which is generated at a time of a rotating movement of the rotation guide 370 by being in contact with the fixing guide 352. The second guide bearing 375 may be positioned on or at a side of the second guide surface 372.

The rotation guide 370 may further include a second rack 374 which may be linked to the second gear 365. A plurality of gear teeth may be formed on the second gear 365 and the second rack 374, and the second gear 365 and the second rack 374 may be geared to each other through the plurality of gear teeth.

With reference to FIG. 19 to FIG. 21, a state in which the flow adjusting device 300 rotates in the second direction to the "second position" at which it is inclined is illustrated. In contrast, in the state of FIG. 15, a position in which the housing main bodies 311 and 312 of the flow adjusting device 300 are laid out, that is, at the "first position" is illustrated.

When the second gear motor 367 rotates, the rotation guide 370 rotates in the vertical direction by linkage of the second gear 365 and the second rack 374. Accordingly, the flow adjusting device 300 performs rotation in the second direction according to the movement of the rotation guide 370. FIG. 19 to FIG. 21 are views illustrating states in which the flow adjusting device 300 is rotated in the upward direction.

When the third fan motor 335 operates, the third fan 330 is driven and at least a portion of air discharged from the second discharge guide 280 may be introduced to the inside portion of the fan housing 310. The introduced air may pass through the third fan 330 and may be discharged to the outside through the second discharge portion 305. Air which is discharged through the second discharge portion 305 may be directed to the upper side and the front side. The terms "front side" may refer to a direction in which the second discharge portion 305 directs the air.

In a state in which the flow adjusting device 300 is in the second position, rotation in the first direction may be performed. As described above, rotation in the first direction may be performed by linkage of the first gear 360 and the first rack 276.

According to this operation, air which is discharged from the air cleaner 10 is not simply directed in the upward direction but may be directed in the frontward direction as well, and thus, air flow may be directed from the air cleaner 10 to a relatively distant space. A blowing force of air which is discharged may be increased as the additional third fan 330 is provided in the flow adjusting device 300. In addition, as the flow adjusting device 300 is capable of performing rotation in the first direction, air may be discharged to the front side of the air cleaner 10, and accordingly, air flow may be provided toward a relatively large indoor space.

The flow adjusting device 300 may be selectively operated according to an operation mode of the air cleaner 10. In a case in which the air cleaner 10 is operated in a general operation mode (first operation mode), the flow adjusting device 300 is in the first position which is laid out, as illustrated in FIG. 1 and FIG. 15. A plurality of independent air flows may be formed by driving the first blowing device 100 and the second blowing device 200.

In other words, when the first blowing device 100 is operated, suction of the air is performed through the first suction portion 102 and the base suction portion 103 and the air is discharged through the first discharge portion 105 by passing through the first filter 120 and the first fan 160. When the second blowing device 200 is operated, suction of the air is performed through the second suction portion 202 and the base suction portion 103 and the air is discharged via the third fan 330 by passing through the second filter 220 and the second fan 260. Air may be discharged in the upward direction through the second discharge portion 305. At this time, the third fan 330 may turn off. Naturally, the third fan 330 may be driven in order to strongly discharge the air flow through the second discharge portion 305.

In contrast, in a case in which the air cleaner 10 is operated in a flow conversion mode (second operation mode), as illustrated in FIG. 19 to FIG. 21, the housing main bodies 311 and 312 of the flow adjusting device 300 may project upwardly. Operation of the first blowing device 100 and the second blowing device 200 in the flow conversion mode may be the same as the operation of the first blowing device 100 and the second blowing device 200 in the general mode.

The third fan 330 may be operated, and accordingly, at least a portion of air having passed through the second fan 260 may be introduced into the third fan housing 310. At least a portion of the introduced air may be discharged toward the front side of the air cleaner 10 while passing through the third fan 330. In a state in which the flow adjusting device 300 is in the first position, air flow may be directed in the upward direction.

For convenience of description, components described above may be defined as follows.

Both the first filter 120 and the second filter 220 may be referred to as a "filter", both the first filter frame 130 and the second filter frame 230 may be referred to as a "filter frame", the filter fan housing 150 and the second fan housing 250 may be referred to as a "fan housing", and both the first fan 160 and the second fan 260 may be referred to as a "fan".

Figure 22:
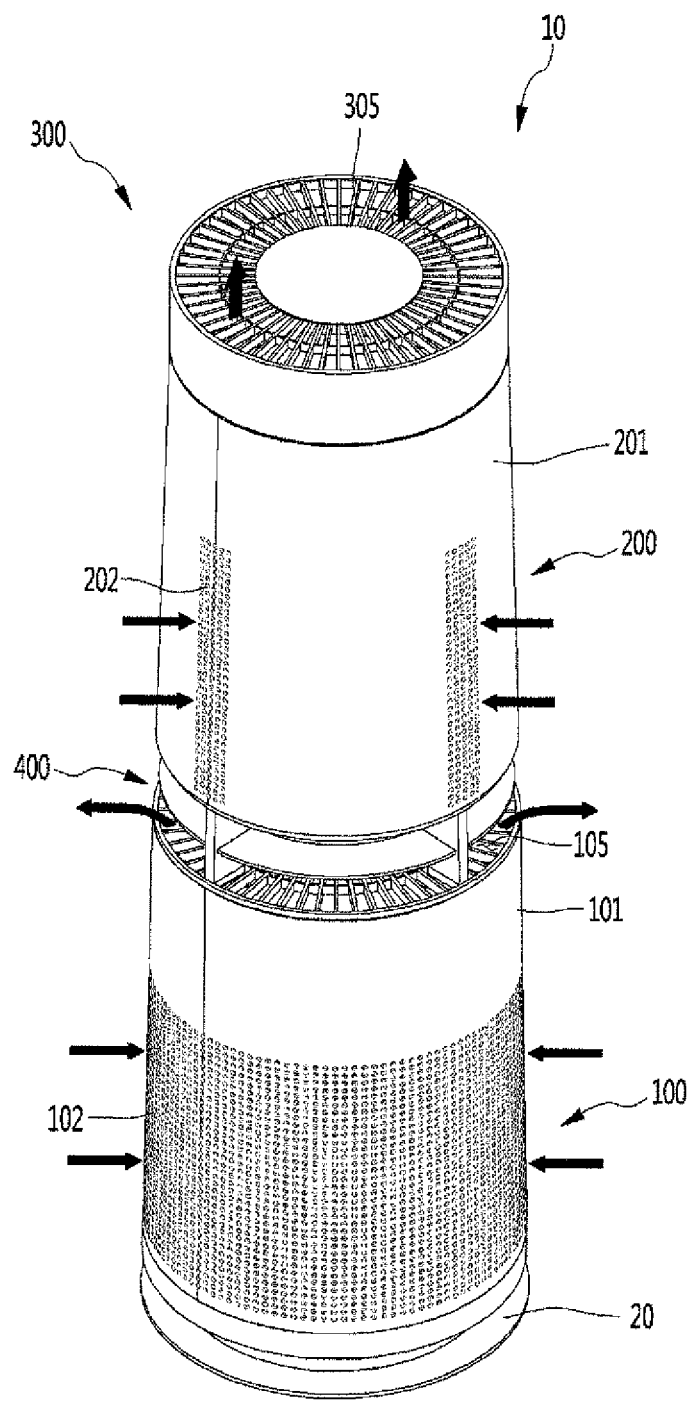
FIG. 22 to FIG. 24 are views illustrating an air flow state in the air cleaner of FIG. 1.
Figure 23:
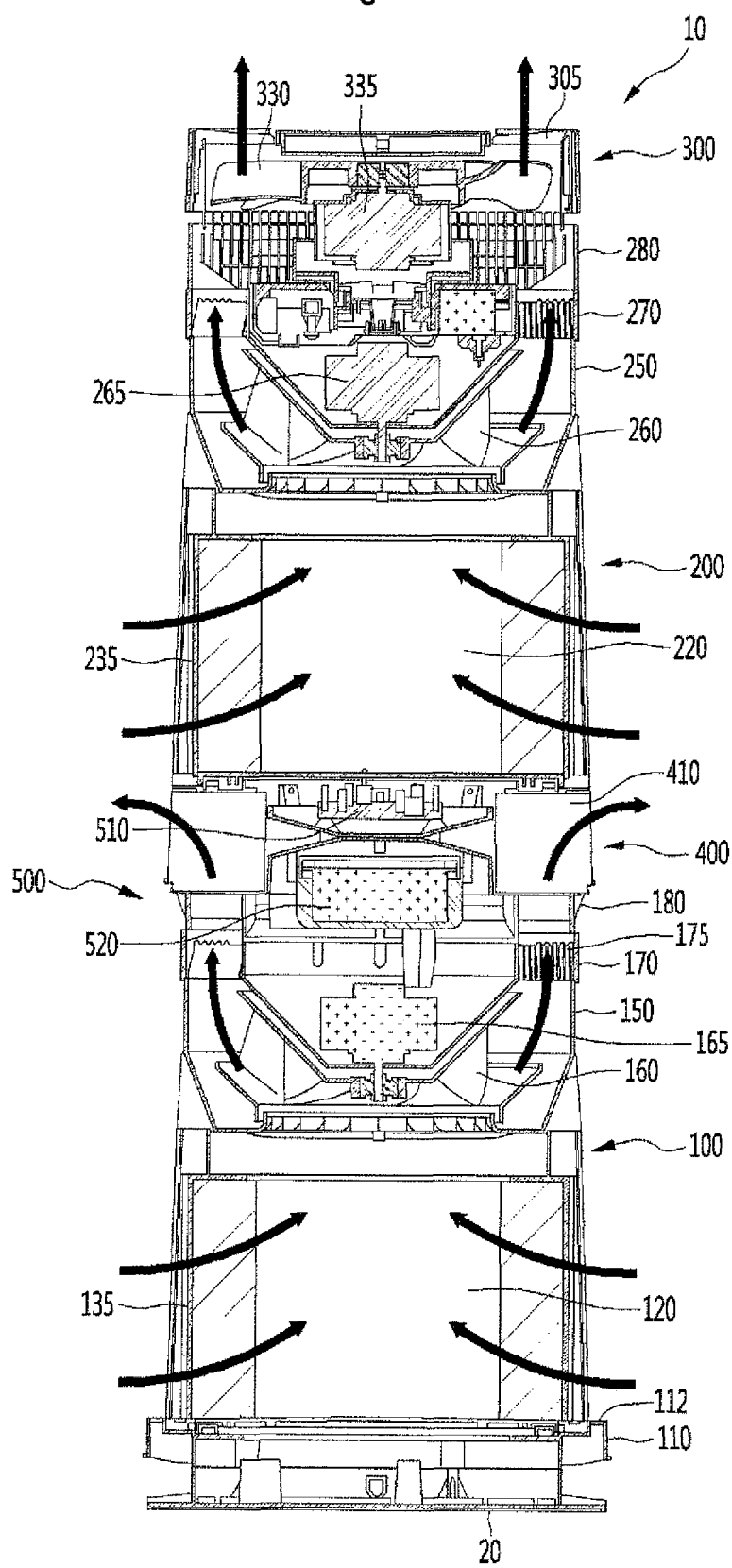
Figure 24:
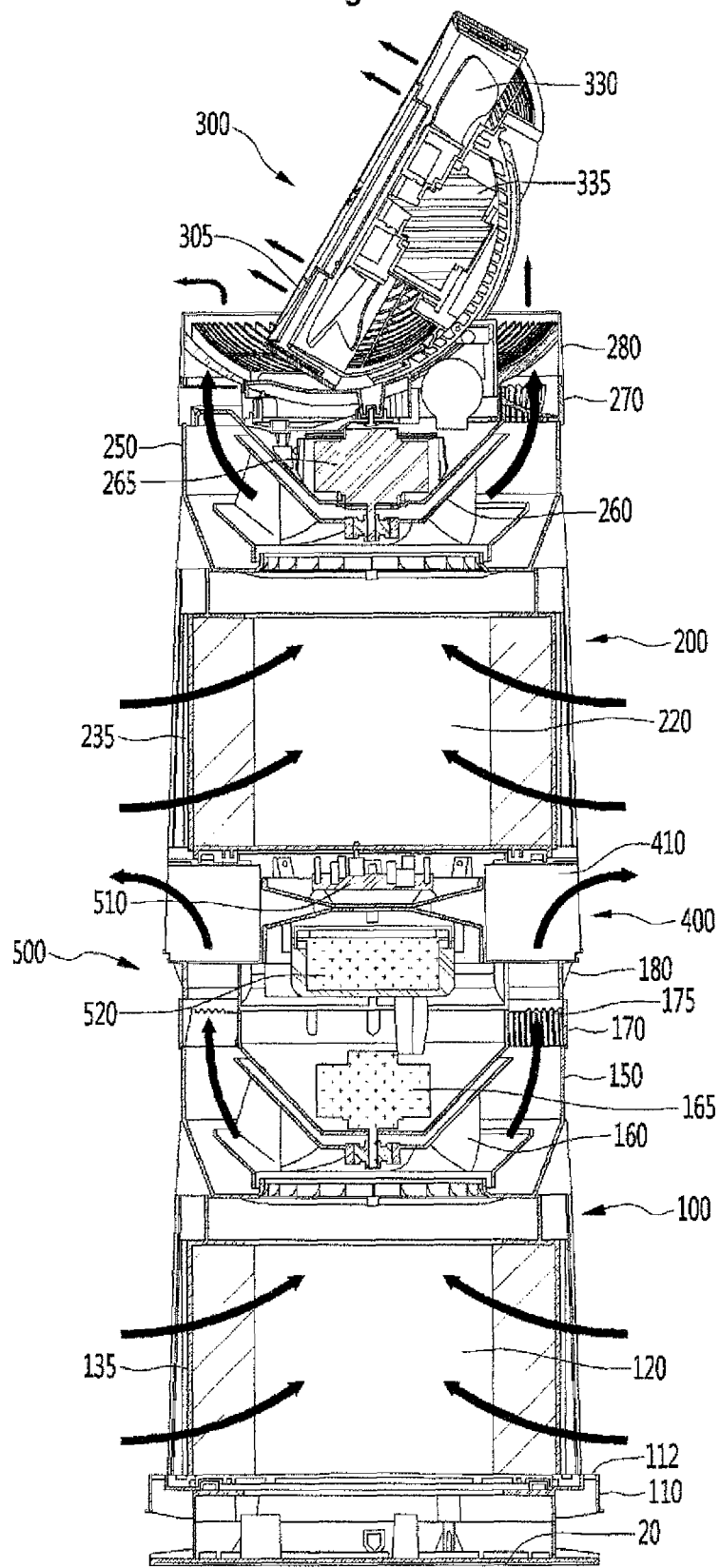

FIG. 22 to FIG. 24 are views illustrating an air flow state in the air cleaner of FIG. 1. First, a flow of air according to operation of the first blowing device 100 is described hereinafter. When the first fan 160 is driven, indoor air is suctioned into the inside of the first case 101 through the first suction portion 102 and the base suction portion 103. The suctioned air passes through the first filter 120 and foreign materials in the air may be filtered in this process. In the process of the air passing through the first filter 120, air may be suctioned in a radial direction of the first filter 120, filtered, and then flow in the upward direction.

The air which has passed through the first filter member 120 may flow to the upper side in the radial direction while passing through the first fan 160 and stably flow in the upward direction while passing through the first air guide 170 and the second air guide 180. Air passing through the first air guide 170 and the second air guide 180 may pass by the first discharge guide 190 and flow in the upward direction through the first discharge portion 105. Air which is discharged through the first discharge portion 105 may be guided by the dividing plate 430 which may be positioned at an upper side of the first discharge guide 190, and thus, may be discharged outside of the air cleaner 10.

When the second fan 260 is driven, indoor air may be suctioned into the inside of the second case 201 through the second suction portion 202, the suctioned air may pass through the second filter 220, and in this process, foreign materials in the air may be filtered. In the process of the air passing through the second filter 220, air may be suctioned in the radial direction of the first filter 120, filtered, and then flow in the upward direction.

Air having passed through the second filter 220 may flow to the upper side in the radial direction while passing through the second fan 160, and stably flow in the upward direction while passing through the third air guide 270 and the second discharge guide 280. Air having passes through the third air guide 270 and the second discharge guide 280 may be discharged through the second discharge portion 305 via the flow adjusting device 300.

The flow adjusting device 300 may be rotatable in the vertical direction by the second guide. For example, as illustrated in FIG. 22 and FIG. 23, when the flow adjusting device 300 is in the first position, air which is discharged from the flow adjusting device 300 may flow in the upward direction. In contrast, when the flow adjusting device 300 is in the second position, air which is discharged from the flow adjusting device 300 may flow to the upper side in the frontward direction. A blowing amount of air which is discharged from the air cleaner 10 may be increased and purified air may be supplied from the air cleaner 10 to a distant position or space, by the flow adjusting device 300.

That is, when the third fan 330 of the flow adjusting device 300 is driven, at least a portion of air discharged from the second discharge guide 280 may be introduced to the inside of the third fan housing 310. The introduced air may pass through the third fan 330 and then may be discharged to the outside through the second discharge portion 305.

The flow adjusting device 300 may be rotated in the lateral direction by the first guide to the second position. For example, in a case in which the flow adjusting device 300 is directed to the upward side in the frontward direction, air which is discharged through the second discharge portion 305 may flow to the upper side in the frontward direction. In contrast, in a case in which the flow adjusting device 300 directs air to the upper side in the rearward direction, air which is discharged through the second discharge portion 305 may flow to the upper side in the rearward direction.

By this operation, air flow may be directed from the air cleaner 10 to a relatively distant space, as air which is discharged from the air cleaner 10 is not directed simply in the upward direction, but rather is directed in the frontward direction. A blowing force of the discharged air may be increased, as the additional third fan 330 may be provided in the flow adjusting device 300.

Figure 25:
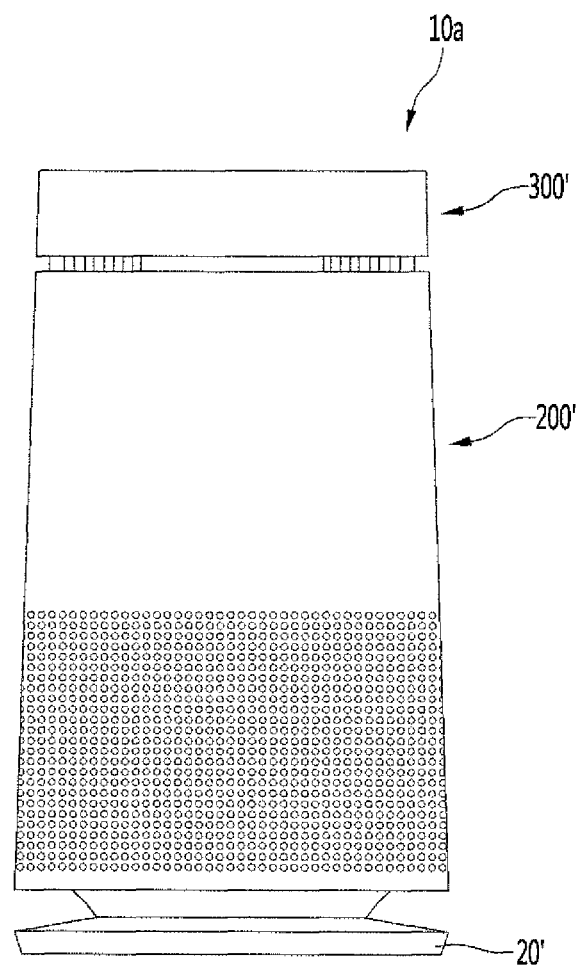
FIG. 25 and FIG. 26 are views of an air cleaner according to another embodiment.
Figure 26:
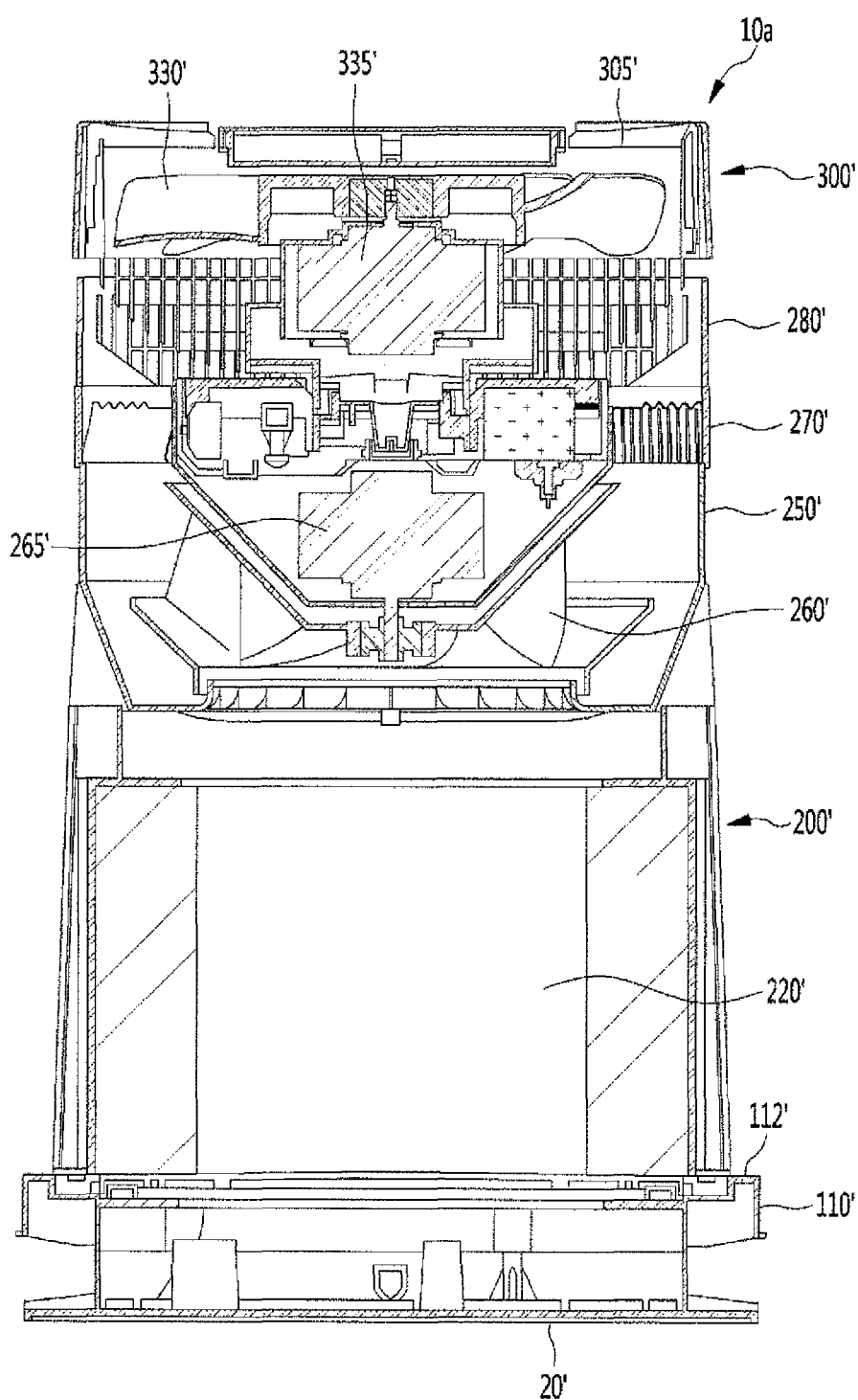

FIG. 25 and FIG. 26 are views of an air cleaner according to another embodiment. With reference to FIG. 25 and FIG. 26, the air cleaner 10a according to this embodiment may include a single blowing device 200' and a flow adjusting device 300'. When compared with the previous embodiment, the air cleaner 10a may include the second blowing device 200 and the flow adjusting device 300 without the first blowing device 100.

The single blowing device 200' may include a base 20', which may be placed on the ground, and a suction grill 110', which may be provided at an upper side of the base 20 and have a suction port 112'. The base 20' and the suction grill 110' may be the same or similar to the base 20 and the suction grill 110 of the first blowing device 100, and thus, repetitive disclosure has been omitted.

The single blowing device 200' may include a filter 260' which may be provided at an upper side of the suction grill 110', a fan 260', a fan motor 265', a fan housing 250', an air guide device or guide 270', and a discharge guide device or guide 280'. The air cleaner 10a may include a flow adjusting device 300', which may have a discharge portion or outlet 305'. A flow adjusting device 300' may include a third fan 330' and a third fan motor 335'.

The single blowing device 200' and the flow adjusting device 300' may be the same or similar to the first blowing device 200 and the flow adjusting device 300 of the previous embodiment. In a case in which a size of the indoor space is not large, a sufficient air cleaning ability may be achieved by operating the air cleaner which includes the single blowing device and the flow adjusting device.

The PCB device described with respect to the previous embodiment may be provided inside of the base 20'. In this case, an additional space for installing the PCB device is not required, and accordingly, space utilization of the air cleaner may be improved.

Figure 27:
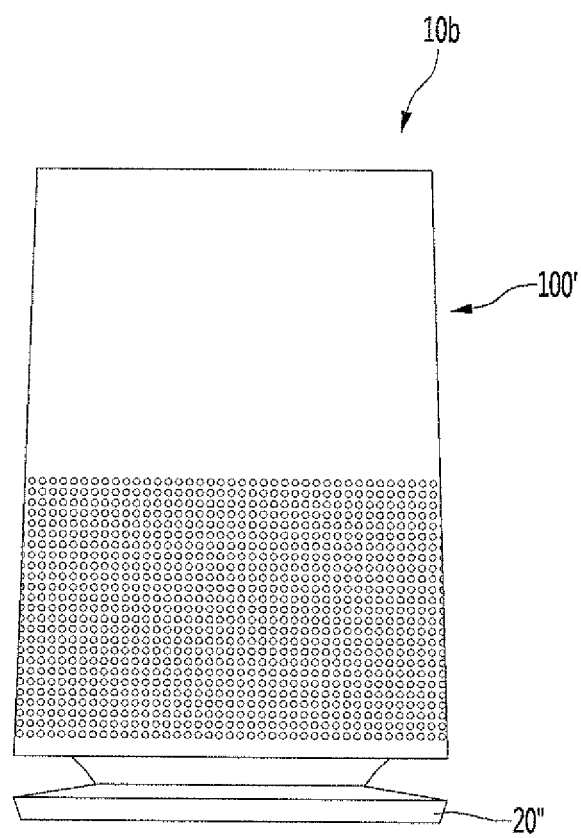
FIG. 27 and FIG. 28 are views of an air cleaner according to yet another embodiment.
Figure 28:
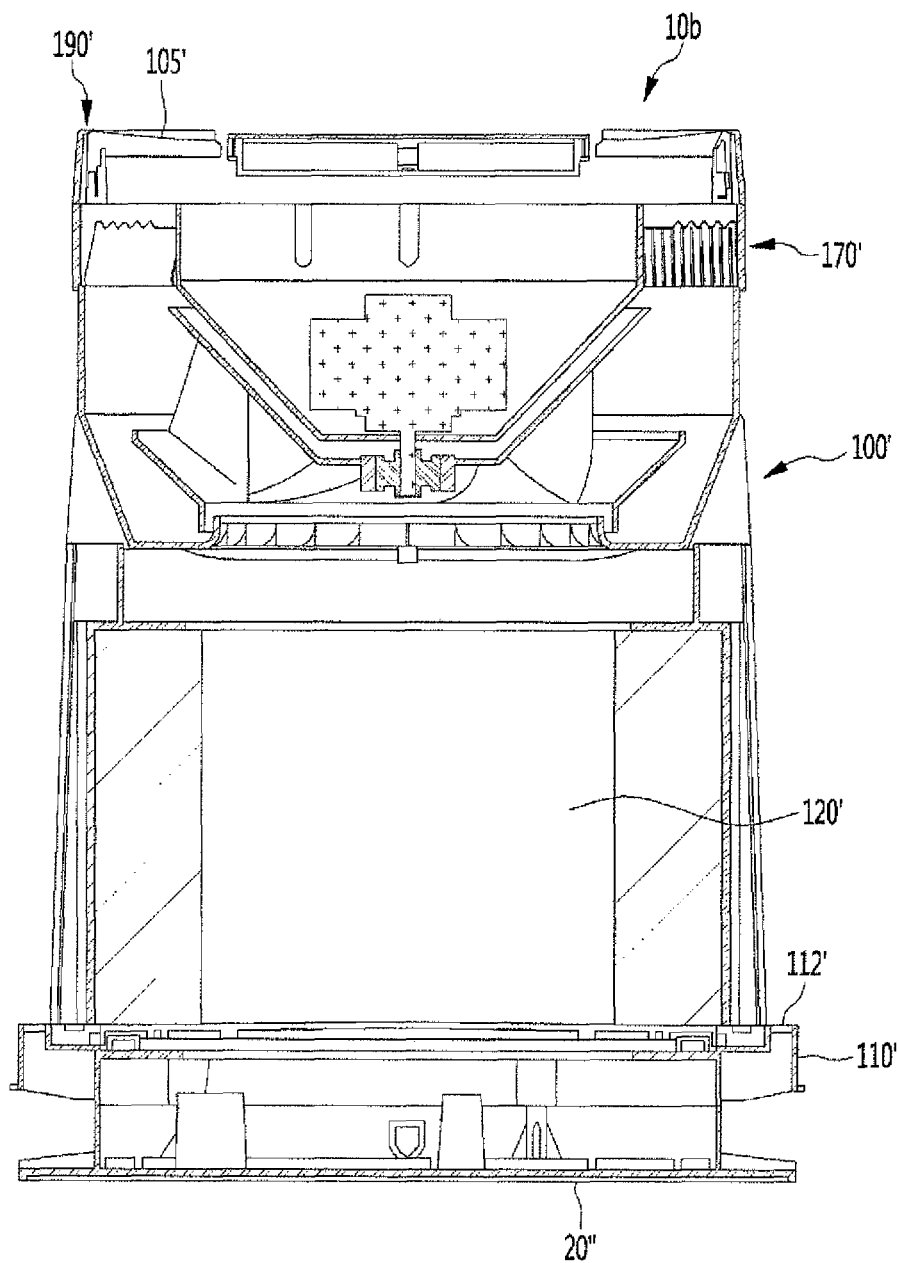

FIG. 27 and FIG. 28 are views of an air cleaner according to yet another embodiment. With reference to FIG. 27 and FIG. 28, the air cleaner 10b according to this embodiment may include a single blowing device 100'. When comparing with the embodiment of FIG. 1, the air cleaner 10b may include the first blowing device 100 without the second blowing device 200 and the flow adjusting device 300.

The single blowing device 100' may include a base 20", a suction grill 100' having a suction portion or inlet 112', a filter 120', a fan 160', a fan housing 150', an air guide device or guide 170', and a discharge guide device or guide 190' having a discharge portion or outlet 105'.

The single blowing device 100' may be the same or similar to the first blowing device 100 of the embodiment of FIG. 1, and thus, repetitive disclosure has been omitted. In a case in which a size of the indoor space is not large, a sufficient air cleaning ability may be achieved by operating the air cleaner which may include the single one blowing device.

The PCB device described in the embodiment of FIG. 1 may be provided inside of the base 20". In this case, an additional space for installing the PCB device is not required, and accordingly, space utilization of the air cleaner may be improved.

Figure 29:
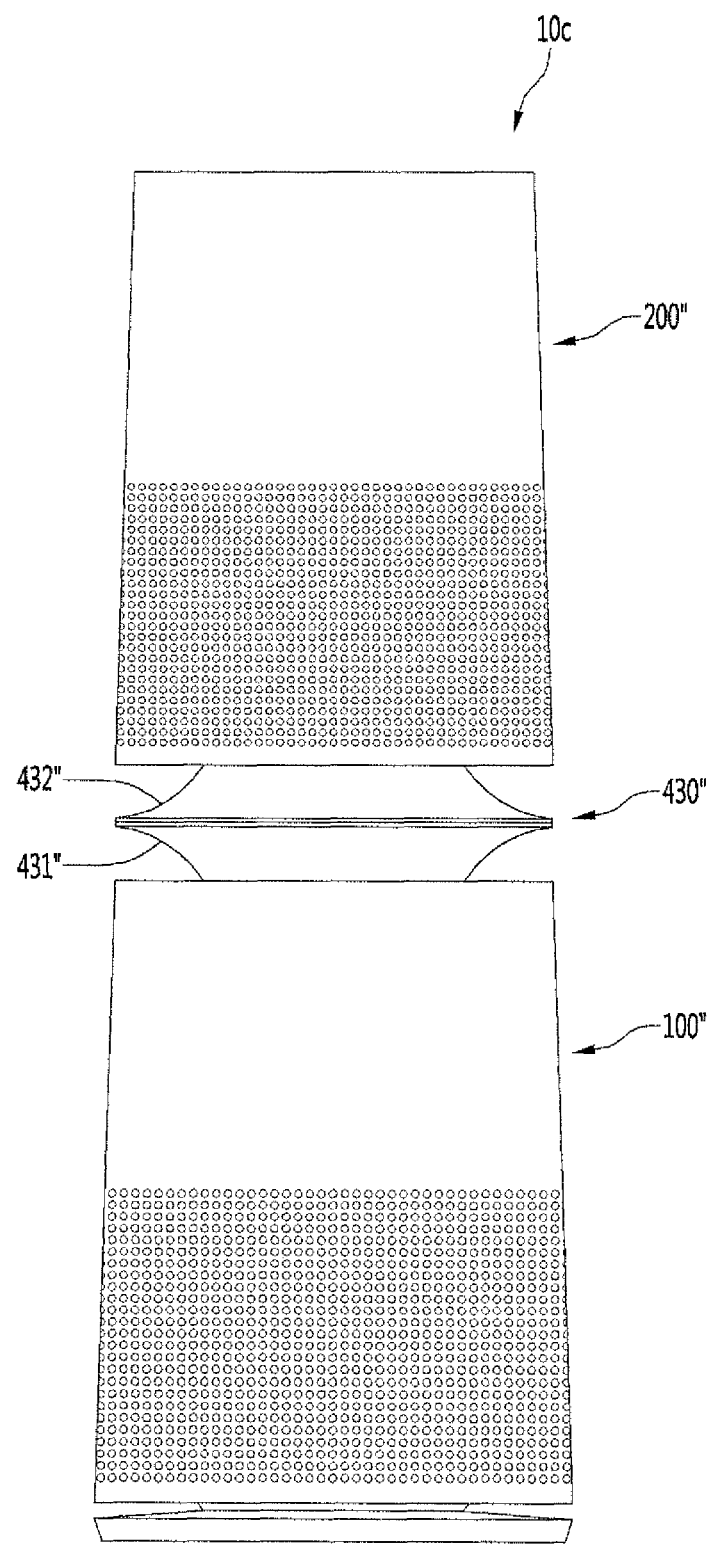
FIG. 29 and FIG. 30 are views of an air cleaner according to still another embodiment.
Figure 30:
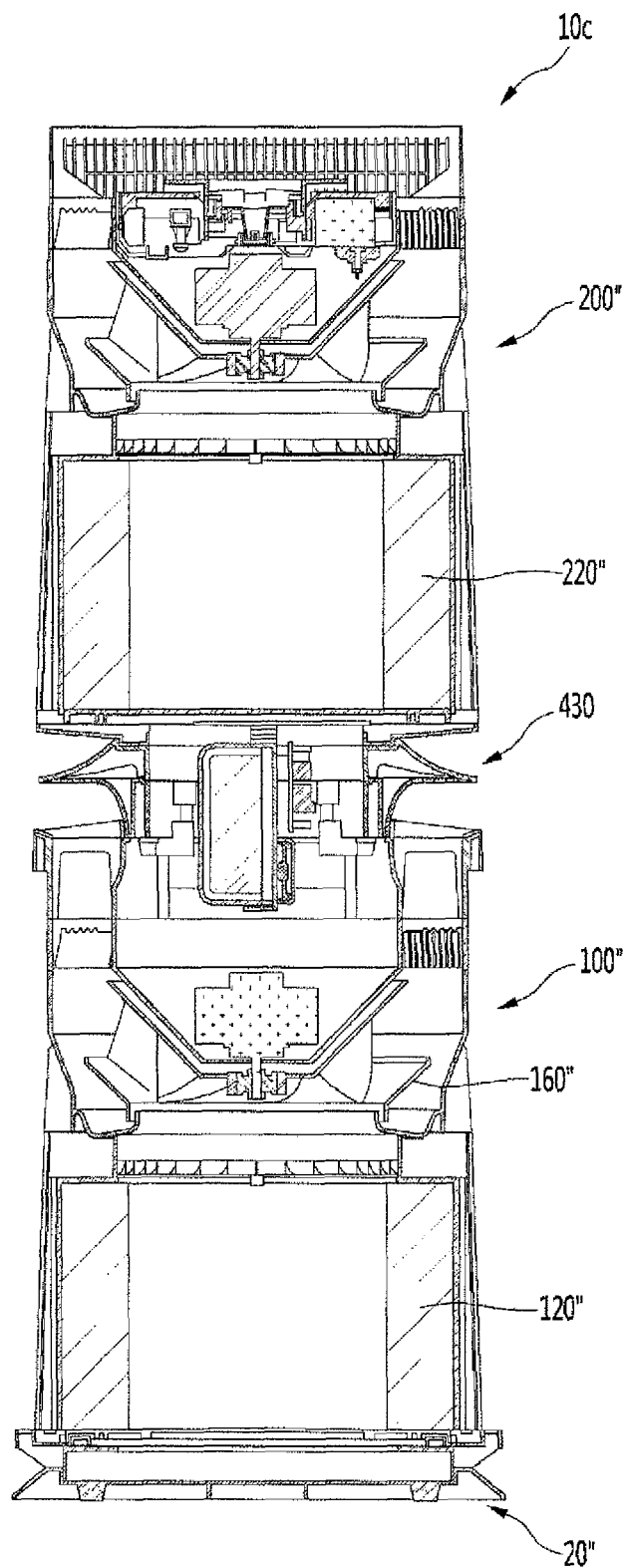

FIG. 29 and FIG. 30 are views of an air cleaner according to still another embodiment. With reference to FIG. 29 and FIG. 30, an air cleaner 10c according to this embodiment may include a first blowing device 100" and a second blowing device 200". When compared with the embodiment of FIG. 1, the air cleaner 10c may include the first blowing device 100 and the second blowing device 200 without the flow adjusting device 300.

A dividing plate 430" that divides an air flow which is generated in the first blowing device 100" and the second blowing device 200", respectively, may be provided between the first blowing device 100" and the second blowing device 200". The air cleaner 10c may include a first rounded portion 431", which may be provided at a lower side of the dividing plate 430" and extend rounded to the outside in the radial direction, and a second rounded portion 432", which may be provided at an upper side of the dividing plate 430" and extend rounded to the inside in the radial direction.

The first rounded portion 431" may guide air which is discharged from the first blowing device 100" to the outside in the radial direction. A grasping space portion or space capable of being grasped by a user in order to move the air cleaner 10c may be formed in a space between the second blowing device 200" and the second rounded portion 432".

Embodiments disclosed herein provide an air cleaner capable improving a suction capacity of air suctioned into the air cleaner. In particular, embodiments disclosed herein provide an air cleaner capable of sufficiently suctioning air around a person in a room whether the person in the room is sitting or standing up by including a suction flow path which is directed from a circumferential direction of the air cleaner to an inside thereof and a suction flow path through which air is introduced through an upper portion and a lower portion of the air cleaner.

In addition, embodiments disclosed herein provide an air cleaner capable of discharging air which is discharged from the air cleaner in various directions and sending the discharged air a long distance. In particular, embodiments disclosed herein provide an air cleaner which is capable of easily discharging air toward a surrounding space of a person in a room whether the person in the room in sitting down or standing up by generating a discharge air flow in an upward direction, a frontward direction, and lateral directions of the air cleaner.

Further, embodiments disclosed herein provide an air cleaner capable of guiding air which is discharged from the air cleaner to an outside of the air cleaner and preventing the discharged air from being reintroduced to the air cleaner. Furthermore, embodiments disclosed herein provide art air cleaner a blowing capacity of which may be increased. Also, embodiments disclosed herein provide an air cleaner in which an air guide is provided which allows air passing through a centrifugal fan to flow toward a outlet in an upward direction in a case of adopting a centrifugal fan in order to increase a blowing capacity.

Embodiments disclosed herein provide an air cleaner that improves a purification capacity of a filter and in which replacement of the filter may be easily performed. Embodiments disclosed herein provide an air cleaner in which a filter may be easily installed without an installation space to install the filter in an inside portion of an air cleaner being additionally provided.

An air cleaner according to embodiments disclosed herein may include a cylindrical case and a suction inlet formed along an outer circumferential surface of the case. The air cleaner may include a plurality of blowing devices that generates air flow.

The plurality of blowing devices may include a first blowing device and a second blowing device, which may be vertically arranged, and a dividing device or divider may be provided between the first blowing device and the second blowing device, which blocks air flow through the first blowing device and the second blowing device from each other. The dividing device may include a leg capable of ensuring a discharge space of the first blowing device and a blocking wall to the leg.

The plurality of blowing devices may include a filter member or filter which may be separably and slidably coupled to and supported on a filter frame to be slid and may be converted into a coupled state by an operation of a handle. The filter member may have a cylindrical shape.

The plurality of blowing devices may include a turbo fan that generates air flow. The plurality of blowing devices may include an air guide device or guide that guides air passing through the turbo fan to a discharge outlet. The air guide device may include a plurality of guide ribs which may be arranged in a circumferential direction of the air guide device and guide the air passing through the turbo fan to flow in an axial direction. A projecting portion or projector may be included on a surface of the guide rib.

A PCB assembly may be provided in a divided space between the first blowing device and the second blowing device or an internal space of a base that supports the plurality of blowing devices.

A flow adjusting device may be included, which may be installed or provided on or at a side of the plurality of blowing devices and convert at least a portion of air flow in the air passing through the plurality of blowing device. The flow adjusting device may include an axial flow fan that suctions air in an axial direction and then discharges air in the axial direction. The flow adjusting device may include a rotation guide device or guide that rotates the axial flow fan in a vertical direction or in a lateral direction.

The rotation guiding device may include a first gear assembly that rotates the axial flow fan in the lateral direction. The rotation guiding device may include a second gear assembly that rotates the axial flow fan in the vertical direction.

In a general operation mode of the air cleaner, the flow adjusting device may move to a first position, and in the first position, the axial flow fan may be oriented in a laid out state, that is, a state in which an axial direction of the axial flow fan is a vertical direction. In a flow conversion mode of the air cleaner, the flow adjusting device may move to a second position, and in the second position, the axial flow fan may be in an erected state, that is, in a state in which an axial direction of the axial flow fan is inclined in a frontward direction.

According to embodiments disclosed herein, a suction capacity may be improved as a suction portion may be formed along an outer circumferential surface of a cylindrical case and a structural resistance of the case may not be generated in an air suction process. In particular, a plurality of apertures may be included on the suction portion and a suction flow path which is directed to an inside portion of the air cleaner may be formed in 360 degree directions relative to the air cleaner, as a plurality of apertures may be formed evenly over an entire outer circumferential surface of the case. Finally, a suction area of air may be increased and air around a person in a room may be sufficiently suctioned where the person in the room in sitting down or standing up.

The suction portion may include a first suction portion or inlet which may be provided in a first case, a third suction portion or inlet which may be provided in a second case, and a second suction portion or inlet which may be provided in a base side, and thus, may be provided in the axial direction from a lower portion to an upper portion of the case. Accordingly, a suction capacity of the indoor space may be increased, as air at a lower portion of an indoor space and air of the indoor space at a relatively high position relative to the air cleaner may be suctioned into the air cleaner.

In addition, discharge of air in an upward direction may be guided through the second blowing device and discharge of air in a frontward direction may be guided by the flow adjusting device which may be provided on or at an upper side of the second blowing device. Discharge of air in a lateral direction may be guided, in a process of rotating of the flow adjusting device. Finally, an air cleaning function of the indoor space may be improved as discharge of air in various directions may be guided relative to the air cleaner and a discharge air flow may be formed to extend a long distance from the air cleaner. A discharge air flow may be easily generated toward a circumferential space of a person in a room whether the person in the room is sitting down or standing up.

In addition, air which is discharged through the first blowing device may be prevented from being introduced to the second blowing device again, as a blocking wall that extends in a transverse direction or a radial direction may be provided in the dividing device to perform division between the first blowing device and the second blowing device. The air which is discharged through the first blowing device may be guided to the outside of the air cleaner, by the blocking wall.

A blowing capacity of the air cleaner may be improved as the plurality of blowing devices may be provided. Further, the air which may flow in the radial direction through the centrifugal fan may be easily guided toward a discharge portion in the upward direction, as the centrifugal fan that increases a blowing capacity of the air cleaner and the air guide device which may be disposed on or at an outlet side of the centrifugal fan may be provided.

A phenomena that interference with each other between air flows may be prevented as air flows which are independent from each other may be generated by the first blowing device and the second blowing device. Accordingly, an air flowing capacity may be improved.

The suction area may be increased as air may be introduced to the inside portion of the filter member from all directions outside of the filter by the filter being provided in a cylindrical shape. Accordingly, an air cleaning capacity of the filter may be improved.

Assembly or disassembly of the filter may be easily performed as the filter may be slid toward or away from the filter frame in the radial direction.

A blowing amount may be increased as the turbo fan which suctions air in the axial direction and then discharges the air in the radial direction may be included in the blowing fan. Flow loss may be reduced and noise may be reduced, as the air guide in which the guide rib is included may be provided in or at an outlet side of the turbo fan. Vortex generation may be reduced and air flow toward the discharge portion may be smoothly performed, as the projecting portion may be provided in the guide rib.

Space utilization may be improved as a PCB assembly may be provided in a divided space between the first blowing device and the second blowing device or in an internal space of a base which supports the blowing device. Air which is discharged from the air cleaner may be discharged a long distance, as air may be discharged toward the front side by the flow adjusting device which converts the air flow being provided on one side of the blowing device.

The operation of the flow adjusting device may be smoothly performed, as movement of the flow adjusting device may be guided by the first gear assembly and the second gear assembly. In addition, a user may intuitively confirm a current operation mode of the air cleaner, even if the user does not confirm a display device of the air cleaner, as a position of the flow adjusting device may be changed according to the operation mode of the air cleaner.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air cleaner, comprising:
    a first air cleaning module including a first fan, a first filter, a first inlet through which air is suctioned into the first filter, and a first outlet through which air passing through the first fan is discharged;
    a second air cleaning module disposed on the first air cleaning module, the second air cleaning module including a second fan, a second filter, a second inlet through which air is suctioned into the second filter and a second outlet through which air passing through the second fan is discharged; and
    an air flow controller disposed on the second air cleaning module, the air flow controller including a housing, a third inlet through air discharged from the second outlet is introduced into the housing and a third outlet through which air is discharged from the housing, wherein the air flow controller moves such that a flow direction of air discharged through the third outlet is changed.

2. The air cleaner of claim 1, wherein the second air cleaning module further includes a discharge grill having the second outlet, and wherein the air flow controller further includes an introduction grill laid on the discharge grill, the introduction grill having the third inlet.

3. The air cleaner of claim 2, wherein the second fan includes a centrifugal fan.

4. The air cleaner of claim 3, wherein the second air cleaning module further includes a discharge guide including:
  a discharge inner wall that defines an inner cylindrical surface of the discharge guide; and
  a discharge outer wall that defines an outer cylindrical surface of the discharge guide, the discharge outer wall being configured to surround the discharge inner wall.

5. The air cleaner of claim 4, wherein the discharge grill extends from the outer cylindrical surface of the discharge inner wall to the inner cylindrical surface of the discharge outer wall.

6. The air cleaner of claim 2, wherein the discharge grill is formed in a concave shape in the downward direction, and wherein the introduction grill is formed in a convex shape in the downward direction.

7. The air cleaner of claim 1, wherein the air flow controller further includes a third fan provided within the housing.

8. The air cleaner of claim 7, wherein the first and second air cleaning modules and the air flow controller are arranged in a vertical direction.

9. The air cleaner of claim 8, wherein the first, the second and the third fan are positioned on a same axis in a longitudinal direction.

10. The air cleaner of claim 1, further comprising a divider provided between the first and the second air cleaning modules.

11. The air cleaner of claim 10, wherein the divider includes:
  a plurality of legs that spaces apart the first and the second air cleaning modules from each other; and
  a blocking wall provided between the plurality of legs, the blocking wall extending in a radial direction.

12. The air cleaner of claim 1, wherein the air flow controller is movable from a first position to a second position, and wherein the first position is a position in which a top of the air flow controller extends substantially parallel to a top of the second air cleaning module in height, and wherein the second position is a position at which the top of the air flow controller is at an angle with respect to the top of the second air cleaning module.

13. The air cleaner of claim 1, wherein the air flow controller performs a first rotation in lateral directions at the first position or the second position.

14. The air cleaner of claim 13, wherein the air flow controller includes a first guide to guide the first rotation, the first guide including:
  a first gear including a first gear shaft; and
  a first gear motor coupled with the first gear shaft.

15. The air cleaner of claim 14, wherein the second air cleaning module further includes an air guide coupled with a bottom of the air flow controller, the air guide including a first rack interlocked with the first gear.

16. The air cleaner of claim 15, wherein the first rack has a curvature in a circumferential direction.

17. The air cleaner of claim 15, wherein the air guide is provided between the second fan and the second outlet.

18. The air cleaner of claim 1, wherein the air flow controller includes a second guide to guide the second rotation, the second guide including a fixed guide having a second gear and a second gear motor coupled with the second gear.

19. The air cleaner of claim 18, wherein the air flow controller further includes a rotational guide having a second rack that interlocks with the second gear.

20. The air cleaner of claim 1, wherein the second air cleaning module further includes a cylindrical case in which the second inlet is formed, wherein the second inlet includes a plurality of through-holes arranged in a circumferential direction.

* * * * *